United States Patent
Park

(10) Patent No.: US 10,401,901 B2
(45) Date of Patent: Sep. 3, 2019

(54) WEARABLE DEVICE

(71) Applicant: MotionVirtual, Inc., San Francisco, CA (US)

(72) Inventor: JunHo Park, Gyeonggi-do (KR)

(73) Assignee: MotionVirtual, Inc., San Francisco, CA (US)

( * ) Notice: Subject to any disclaimer, the term of this patent is extended or adjusted under 35 U.S.C. 154(b) by 0 days.

(21) Appl. No.: 15/757,121

(22) PCT Filed: Aug. 25, 2016

(86) PCT No.: PCT/KR2016/009418
§ 371 (c)(1),
(2) Date: May 29, 2018

(87) PCT Pub. No.: WO2017/039225
PCT Pub. Date: Mar. 9, 2017

(65) Prior Publication Data
US 2018/0299922 A1     Oct. 18, 2018

(30) Foreign Application Priority Data

Sep. 3, 2015   (KR) .................. 10-2015-0125011

(51) Int. Cl.
*G06F 1/16*     (2006.01)
*H04N 9/31*     (2006.01)
(Continued)

(52) U.S. Cl.
CPC .............. *G06F 1/16* (2013.01); *A61B 5/1114* (2013.01); *A61B 5/1126* (2013.01); *A61B 5/489* (2013.01); *A61B 5/6803* (2013.01); *A61B 5/6806* (2013.01); *A61B 5/7475* (2013.01); *G06F 3/011* (2013.01); *G06F 3/017* (2013.01); *G06F 3/03* (2013.01); *G06F 3/0425* (2013.01); *G06K 19/07762* (2013.01); *H04N 9/3173* (2013.01);
(Continued)

(58) Field of Classification Search
CPC ....... G06F 1/16; G06F 3/03; G06K 19/07762; H04W 4/80
See application file for complete search history.

(56) References Cited

U.S. PATENT DOCUMENTS 8,570,273 B1   10/2013   Smith
8,773,512 B1   7/2014   Rafii
(Continued)

FOREIGN PATENT DOCUMENTS

JP   2004255212 A   4/2006
JP   2006102110 A   4/2006
(Continued)

OTHER PUBLICATIONS

International Search Report and Written Opinion of International Application No. PCT/KR2016/009418; dated Dec. 14, 2016; 6 pages.

*Primary Examiner* — Omar S Ismail
(74) *Attorney, Agent, or Firm* — Perkins Coie LLP

(57) ABSTRACT

Disclosed is a wearable device. The wearable device includes an optical signal transmission unit configured to transmit optical signals, an optical signal sensing unit configured to receive reflected optical signals, a data processing unit configured to process the reflected optical signals, and a coordinate generating unit configured to generate 3-dimensional coordinate from the processed data.

18 Claims, 9 Drawing Sheets

(a)

(b)

(51) Int. Cl.

| | | |
|---|---|---|
| *G06F 3/03* | (2006.01) | |
| *H04W 4/80* | (2018.01) | |
| *A61B 5/00* | (2006.01) | |
| *G06K 19/077* | (2006.01) | |
| *A61B 5/11* | (2006.01) | |
| *G06F 3/01* | (2006.01) | |
| *G06F 3/042* | (2006.01) | |
| *A61B 5/026* | (2006.01) | |

(52) U.S. Cl.
CPC ......... *H04N 9/3182* (2013.01); *H04N 9/3194* (2013.01); *H04W 4/80* (2018.02); *A61B 5/0261* (2013.01)

(56) References Cited

U.S. PATENT DOCUMENTS

| | | | |
|---|---|---|---|
| 9,367,651 B2 | 6/2016 | Algreatly | |
| 9,582,076 B2 | 2/2017 | Kienzle et al. | |
| 9,760,214 B2 | 9/2017 | Li | |
| 2007/0106172 A1* | 5/2007 | Abreu | A61B 5/0002 600/549 |
| 2007/0273504 A1* | 11/2007 | Tran | A61B 5/0022 340/539.12 |
| 2009/0312817 A1* | 12/2009 | Hogle | A61B 5/0492 607/54 |
| 2010/0103104 A1* | 4/2010 | Son | G06F 3/014 345/158 |
| 2011/0007035 A1* | 1/2011 | Shai | G06F 3/014 345/179 |
| 2012/0075173 A1 | 3/2012 | Ashbrook et al. | |
| 2012/0095352 A1* | 4/2012 | Tran | A61B 5/0022 600/490 |
| 2012/0316459 A1* | 12/2012 | Abreu | A61B 5/0002 600/549 |
| 2013/0346168 A1 | 12/2013 | Zhou et al. | |
| 2014/0039309 A1* | 2/2014 | Harris | A61B 5/7282 600/431 |
| 2014/0098018 A1 | 4/2014 | Kim et al. | |
| 2014/0135612 A1* | 5/2014 | Yuen | A61B 5/02405 600/407 |
| 2014/0204191 A1 | 7/2014 | Takai et al. | |
| 2014/0278220 A1* | 9/2014 | Yuen | G01B 21/16 702/150 |
| 2014/0297218 A1* | 10/2014 | Yuen | G01B 21/16 702/141 |
| 2015/0099941 A1* | 4/2015 | Tran | A61B 5/7214 600/300 |
| 2015/0117708 A1 | 4/2015 | Guigues et al. | |
| 2015/0122018 A1* | 5/2015 | Yuen | G01B 21/16 73/384 |
| 2015/0157262 A1 | 6/2015 | Schuessler | |
| 2015/0186708 A1 | 7/2015 | Katz | |
| 2015/0338916 A1 | 11/2015 | Priyantha et al. | |
| 2015/0382105 A1 | 12/2015 | Thompson et al. | |
| 2016/0007849 A1* | 1/2016 | Krueger | A61B 3/113 600/301 |
| 2016/0015470 A1* | 1/2016 | Border | G02B 27/017 600/117 |
| 2016/0124524 A1 | 5/2016 | Zhao et al. | |
| 2016/0135687 A1* | 5/2016 | Harris | A61B 5/7282 600/431 |
| 2016/0192867 A1* | 7/2016 | Esenaliev | A61B 5/0095 600/316 |
| 2016/0270656 A1* | 9/2016 | Samec | A61B 3/085 |
| 2016/0287166 A1* | 10/2016 | Tran | H04B 1/3827 |
| 2017/0242496 A1 | 8/2017 | Park | |
| 2017/0281026 A1* | 10/2017 | Nick | A61B 5/02416 |
| 2017/0308117 A1* | 10/2017 | Park | G06K 9/00355 |
| 2017/0312614 A1* | 11/2017 | Tran | H04W 4/027 |

FOREIGN PATENT DOCUMENTS

| | | |
|---|---|---|
| JP | 2007128304 A | 5/2007 |
| KR | 1020030017924 A | 3/2003 |
| KR | 1020090079019 A | 7/2009 |
| KR | 1020100047793 A | 5/2010 |
| KR | 1020130092815 A | 8/2013 |
| KR | 101310464 B1 | 9/2013 |
| KR | 101339644 B1 | 12/2013 |
| KR | 101360149 B1 | 2/2014 |
| KR | 1020140062895 A | 5/2014 |
| KR | 101524575 B1 | 6/2015 |
| KR | 1020150083602 A | 7/2015 |
| WO | WO2016028097 A1 | 2/2016 |
| WO | WO2016060461 A1 | 4/2016 |
| WO | WO2017039225 A1 | 3/2017 |

\* cited by examiner (a)

(b)

(a)

(b)

(a)

(b)

WEARABLE DEVICE

CROSS-REFERENCE TO RELATED APPLICATIONS

This application is a 371 national phase application of PCT application PCT/KR2016/009418 filed Aug. 25, 2016, which in turn claims priority and benefit to Korean National Application 10-2015-0125011 filed Sep. 3, 2015. The disclosure of the above applications are hereby incorporated herein by reference.

BACKGROUND

Field of the Invention

The present invention relates to a wearable device.

Related Art

In a modern society in which use of electronic devices is essential to everyday life, electronic devices respectively include input units. However, among such general input units, 2D input units, such as a keyboard, a mouse and the like, are not greatly improved. Further, portability and convenience of the input units need to be improved.

Thereby, an input unit which may satisfy both portability and convenience is required. Particularly, in order to meet the miniaturization trend of electronic devices, a new input unit needs to process various input values so as to sufficiently use functions of electronic devices as well as to have portability and convenience.

SUMMARY

An object of the present invention is to provide a wearable device which allows a user to conveniently input data using a portable input unit.

Another object of the present invention is to provide a wearable device which allows a user to input various kinds of data so as to substitute for input units such as a keyboard and a mouse which exist at present.

Yet another object of the present invention is to provide a wearable device which may maintain precision of input data as well as portability.

Technical objects to be accomplished by the present invention are not limited to the above objects, and other technical objects which are not stated will become apparent to those skilled in the art from the embodiments of the present invention given hereinbelow.

In one embodiment of the present invention, a wearable device includes an optical signal transmission unit configured to transmit optical signals, an optical signal sensing unit configured to receive reflected optical signals, a data processing unit configured to process the reflected optical signals, and a coordinate generating unit configured to generate 3-dimensional coordinate from the processed data.

Embodiments of the present invention may provide effects as below.

First, a user may execute improved data input through a wearable device which may provide both portability and convenience.

Second, the wearable device may replace input means such as a keyboard and a mouse and thus various data input may be executed using only the wearable device without any additional input unit.

Third, the wearable device may maintain precision of data input as well as portability and thus provide improved data input environment to a user.

Effects acquired by the embodiments of the present invention are not limited to the above-stated effects, and other effects which are not stated will be apparent to those skilled in the art from the embodiments of the present invention given hereinbelow. That is, effects which are not intended according to implementation of the present invention will be deduced from the embodiments of the present invention by those skilled in the art.

DESCRIPTION OF THE DRAWINGS

The accompanying drawings, which are included to provide a further understanding of the invention and are incorporated in and constitute a part of this application, illustrate embodiment(s) of the invention and together with the description serve to explain the principle of the invention. In the drawings.

DETAILED DESCRIPTION

Figure 1:
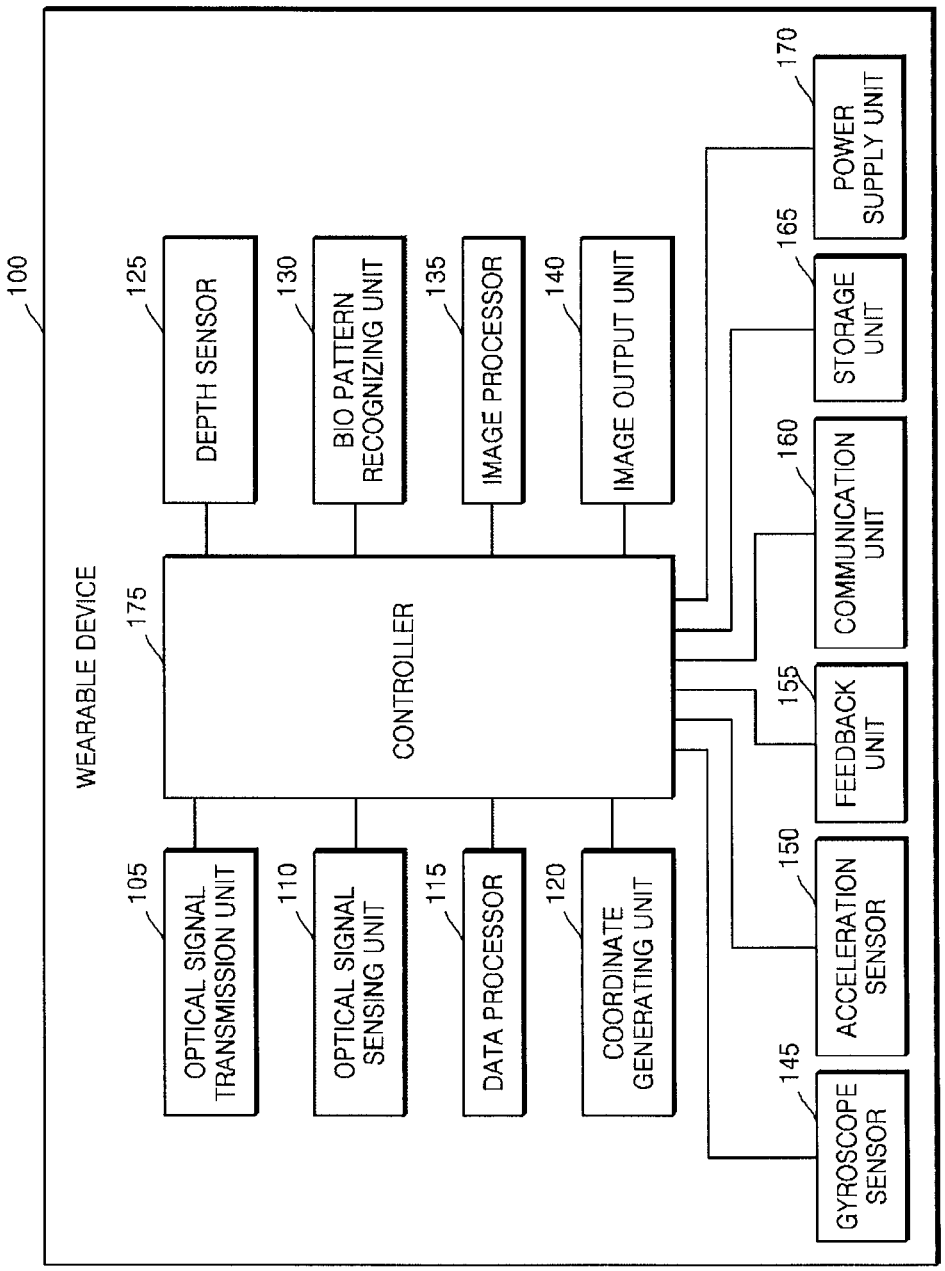
FIG. 1 is a block diagram illustrating configuration of a wearable device in accordance with one embodiment of the present invention.

The terms used in the following description are terms which are generally used at present taking into consideration the functions obtained in accordance with the present invention, and the definitions of these terms may be changed in accordance with the intention of an engineer in the art, a precedent, or advent of new technology. Further, there may be terms selected by the applicant and, in this case, these terms should be defined in the description of the present invention. Therefore, the terms used in the present invention should be defined based on the overall content of this specification.

In embodiments below, elements and features of the present invention are combined into a designated type. The respective elements or features may be selectively considered unless stated otherwise. The respective elements or features may not be combined with other elements or features. Further, some elements and/or features may be combined to produce embodiments of the present invention. A sequence of operations described in the embodiments of the present invention may be changed. Some elements or features in an embodiment may be included in any other embodiment or be replaced by corresponding elements or features of any other embodiment.

In a description of the drawings, procedures or operations which may obscure the spirit of the present invention are not described and procedures or operations which will be apparent to those skilled in the art are omitted.

In the following description of the present invention, it will be understood that the terms "comprising" and "including" do not exclude presence of one or more other elements but mean presence of the corresponding elements, unless stated otherwise. Further, the terms "part", "device" and "module" stated in the description mean a unit to process at least one function or operation and it may be implemented through combination of hardware, software, or hardware and software. Further, if it is stated in the description that an element is "connected to" another element, it may include not only physical connection but also electrical connection and further mean logical connection.

Further, "a" or "an", "one", "the" and their synonyms may indicate both singular and plural, unless stated otherwise in the description of the present invention (particularly, in the claims).

Further, a "user" in the specification may be a wearer or a user of a wearable device and include an engineer to repair the wearable device, but is not limited thereto.

Reference will now be made in detail to the preferred embodiments of the present invention, examples of which are illustrated in the accompanying drawings.

Further, Specific terms used in the embodiments of the present invention are provided only for a better understanding of the present invention and may be changed without departing from the scope and spirit of the invention as disclosed in the accompanying claims.

Hereinafter, prior to description of the embodiments of the present invention, the disclosure of Korean Patent Application No. 10-2014-0108341, Korean Patent Application No. 10-2014-0139081 and Korean Patent Application No. 10-2015-0061522 filed by the same inventor(s) and applicant of the present invention will be referred to. Korean Patent Application No. 10-2014-0108341 proposes a method for generating a 3D model by 3D scanning an object using a wearable device and then sensing movement of a user by adding a pattern to the 3D model, and Korean Patent Application No. 10-2014-0139081 and Korean Patent Application No. 10-2015-0061522 propose a method for sensing movement of a user by analyzing a blood vessel pattern of the user by transmitting/receiving and comparing optical signals.

FIG. 1 is a block diagram illustrating configuration of a wearable device in accordance with one embodiment of the present invention. The wearable device 100 may further include other universal elements in addition to elements shown in FIG. 1, or include a smaller number of elements than the elements shown in FIG. 1. That is, the implementation type and scope of the wearable device 100 are not limited to those shown in FIG. 1.

The wearable device 100 is an input/output means mounted on a part (for example, a hand, a neck, a head, or the like) of a body of a user. The wearable device 100 senses a bio pattern of the user by using various methods and means and generates data and a signal from a result value acquired by processing a sensed result. The generated data and signal may be a target output by the wearable device 100 and may be transmitted to an external device or server. In other words, the wearable device 100 may serve as the input means and the output means for the user.

Hereinafter, various elements of the wearable device 100 will be respectively described. The wearable device 100 in accordance with this embodiment may include an optical signal transmission unit 105, an optical signal sensing unit 110, a data processor 115, a coordinate generating unit 120, a depth sensor 125, a bio pattern recognizing unit 130, an image processor 135, an image output unit 140, a gyroscope sensor 145, an acceleration sensor 150, a feedback unit 155, a communication unit 160, a storage unit 165, a power supply unit 170, and a controller 175. These elements may be connected to one another by wire or wirelessly and transmit/receive data and signals to/from one another. As described above, the elements shown in FIG. 1 are only exemplary elements to form the wearable device 100, and the wearable device 100 may include a greater or smaller number of elements than these elements.

First, the optical signal transmission unit 105 generates and transmits an optical signal. The optical signal transmission unit 105 may generate an optical signal having a specific wavelength, for example, an optical signal having a wavelength of visible rays (approximately, 300 to 700 nm) or infrared rays (approximately 700 to 3000 nm). However, the wavelength of the optical signal generated by the optical signal transmission unit 105 is not limited to such an example and the optical signal transmission unit 105 may also generate a wavelength of far infrared rays having a longer wavelength in addition to the visible rays, near infrared rays, and the infrared rays. According to another embodiment, the optical signal transmission unit 105 may generate an optical signal having consecutive spectrums instead of generating an optical signal having a wavelength in a specific band. The wavelength of the optical signal generated by the optical signal transmission unit 105 will be described below in detail with reference to FIG. 2.

The optical signal transmission unit 105 transmits the generated optical signals. The optical signal transmission unit 105 may transmit the optical signals of a continuous wave type or transmit the optical signals of a non-continuous wave type.

Further, the optical signal transmission unit 105 may transmit an optical signal having a pattern. The pattern means a predetermined shape or type formed when the transmitted optical pattern is projected onto an external surface. For example, the optical signal transmission unit 105 may transmit an optical signal having a stripe pattern. Further, such a pattern of the optical signal may be programmed and pre-stored and an arbitrary pattern recognizable by the wearable device 100 may be used.

As described above, the optical signal transmission unit 105 generates and transmits optical signals through various methods. The optical signal transmission unit 105 may generate and transmit optical signals through various methods by combining wavelengths of optical signals, kinds of optical signals or transmission methods of optical signals. The wearable device 100 may include one or more optical transmission units 105, and a detailed description thereof will be given later in reference to FIG. 2.

The optical signal sensing unit 110 senses optical signals received from the outside. When the optical signals transmitted by the optical signal sensing unit 105 are reflected by an external object (for example, an article or a part of a human body), various physical property values, such as the intensity, wavelength, frequency band, energy and the like of the optical signals, are changed. Hereinafter, the optical signals, the physical properties of which are changed through reflection by an external surface, are referred to as reflected optical signals. The optical signal sensing unit 110 senses reflected optical signals generated upon reflection of the optical signals by the external object.

As the optical signal transmission unit 105 transmits optical signals of various wavelengths, the optical signal sensing unit 110 may sense the optical signals of wavelengths which the optical signal transmission unit 150 may transmit. That is, the optical signal sensing unit 110 may sense an optical signal of a visible light wavelength, an optical signal of a near infrared light wavelength, an optical signal of a far infrared light wavelength and the like, and the wavelength detected by the optical signal sensing unit 110 is not limited to such exemplary bands similarly to the above description.

The data processor 115 processes the optical signals received by the optical signal sensing unit 110 and generates reception data. A data processing procedure by the data processor 115 may include a process of digitalizing analog signals, i.e., the optical signals received by the optical sensing unit 110. A process of generating the reception data through data processing may be carried out at constant periods or carried out according to control instructions from the controller 175 of the wearable device 100.

If the object is a part of a human body, the reception data generated by the data processor 115 may include information regarding blood vessels of the object. That is, as will be described later in detail, the optical signals transmitted by the optical signal transmission unit 105 are reflected, scattered and absorbed by blood vessels of the object and thus, physical property values of the optical signals are changed. Thereby, the data processor 115 may acquire information of arrangement and distribution of the blood vessels of the object by processing the reflected optical signals received by the optical signal sensing unit 110. Hereinafter, among the above-described reception data, reception data if the object is blood vessels will be referred to as blood vessel data for convenience of description.

When the optical signal transmission unit 105, the optical signal sensor 110, and the data processor 115 sense the blood vessel and generate the blood vessel data, at least one of the depth sensor 125 and the bio pattern recognizing unit 130 to be described below may operate together. Although described below in detail, the depth sensor 125 senses the object in 3D to sense a stereoscopic structure, a stereoscopic shape, a stereoscopic location, and the like and the bio pattern recognizing unit 130 recognizes patterns to be verified on the surface of the object to sense visual features including a color, a chroma, brightness, a shape, and the like. The blood vessel data regarding the blood vessel may be configured by 2D information regarding a distribution and a layout of the blood vessel and the blood vessel data which the depth sensor 125 and/or the bio pattern recognizing unit 130 operate together to acquire may be configured by 3D information.

The process of generating the blood vessel data may be performed in 2D or 3D. That is, the optical signal transmission unit 105 and the optical signal sensor 110 may recognize the blood vessel of the object in planar 2D or in stereoscopic 3D. In the case of the 2D, the blood vessel data is converted into 3D data based on a 3D model of the object generated by the depth sensor 125 to be described below. Such a conversion process may be appreciated as a process of determining a curvature of an actual object by determining a degree at which a vein pattern is geometrically distorted by comparing a measured vein pattern of the object with of the vein pattern of a geometric model for the object. In other words, the prestored 3D model of the object is compared with newly measured pattern information, and as a result, the blood vessel data generated in 2D may be converted into 3D. When the 2D data is converted into the 3D data, the 3D data may be coupled to the pregenerated 3D model as a pattern. During such a conversion process, since the 2D data does not include information on a distance, a process of comparing and analyzing the 2D data with the prestored information on the vein pattern may be performed. That is, the information prestored in the wearable device 100 and newly measured 2D data are compared with each other, and as a result, the wearable device 100 may determine what shape the distribution of the veins has in a space. Such a process may be performed based on partial conformity which the wearable device 100 has and a concept of the partial conformity will be described below.

On the contrary, when the blood vessel of the object is fundamentally sensed in 3D, such a conversion process is not required. Therefore, the 3D vessel data may be immediately coupled to the pregenerated 3D model as the pattern. That is, since the 3D blood vessel data has information on the shape and the location of the vein in 3D, an absolute size and the absolute shape for the vein may be immediately determined during the process of coupling the 3D blood vessel data with the 3D model.

As a result of acquiring the blood vessel data in 2D or 3D, the wearable device 100 may recognize the distribution of the vein pattern in detail. Such a concept may be appreciated as a meaning that the wearable device 100 configures a vein map. That is, the wearable device 100 recognizes the vein pattern in 3D to verify all information on a spatial coordinate of a vein branch point, the lengths of respective branches, angles formed by the respective branches at the branch point, the number of branches, and the like in the vein distribution.

Meanwhile, the coordinate generating unit 120 may preferentially compare the vein patterns of a back of the hand and an arm in which the layout of the vein pattern is relatively less changed during comparing the vein pattern with the prestored information. Further, the coordinate generating unit 120 may use even information on a contour or border of a body configuration as information for substituting for the vein pattern together. Sine the information on the contour or border is sensed differently according to an angle at which the wearable device 100 senses the body configuration, the information is analyzed together with the vein pattern information to more efficiently generate a 3D coordinate.

The coordinate generating unit 120 generates the 3D coordinate of the object by using data generated by the data processor 115. The 'object' may be the blood vessel or a part of the body and may be not the body but a thing. That is, the coordinate generating unit 120 generates the 3D coordinate of the object in which a reflection optical signal is generated by the optical signal sensor 110. For example, if the reflection optical signal is generated from the blood vessel pattern of the body of the user, the coordinate generating unit 120 generates the 3D coordinate for the blood vessel pattern of a partial area of the body in which the reflection optical signal is generated. In this case, the 3D coordinate for the blood vessel pattern may have a visualized pattern shape in which the blood vessel pattern is visualized.

As yet another embodiment, when the reflection optical signal is generated from a part (for example, a finger or the arm) of the body of the user, the coordinate generating unit 120 generates the 3D coordinate of the finger or arm which is a part of the body where the reflection optical signal is generated. In this case, the 3D coordinate may be a spatial coordinate of the finger or arm. When described in detail, since the sensed vein pattern covers the surface throughout the body, when the 3D model of the body and the vein pattern are combined and stored, spatial coordinates of organs and components of the body may be independently determined. In other words, a case where the coordinate generating unit 120 determines the 3D coordinate of the object may be appreciated as just determining a spatial location and an angle of the object (for example, the arm of the user) in a broad sense and as determining the 3D coordinate of each of the components (for example, an upper arm and a lower arm, the back of the hand, a joint of the finger of the user, and the like) of each object in a narrow sense. Therefore, according to the 3D coordinates of the components generated by the coordinate generating unit 120, the wearable device 100 may distinguish and recognize the respective organs and components of the body.

The coordinate generating unit 120 may generate the coordinate by distinguishing the body organs by the unit of the joint and according to an implementation example, the coordinate generating unit 120 separates the respective body components even by the larger unit or the smaller unit to generate and recognize the coordinates. According to the embodiment, the wearable device 100 may distinguish and determine at which place and in which shape all specific body components are positioned in the space. Hereinafter, a characteristic that the wearable device 100 may distinguish and recognize the body components is referred to as the partial conformity.

Contents associated with the partial conformity will be described in detail. When the data (blood vessel data) regarding the vein pattern is generated through transmission and reception of the optical signal, the coordinate generating unit 120 concatenates and determines which part among the prestored body components the measured object is. That is, since the wearable device 100 may distinguish the respective components of the body, the measured body component conforms to the prestored information to first determine which component is measured. After the partial conformity process is performed, the coordinate generating unit 120 compares a shape and a degree in which the prestored vein pattern is distorted in the space with respect to the corresponding body component to analogize the shape and the distance of the corresponding component in the space. When the 2D data is scanned, the shape, the distance, and the like of the object may be together determined while the partial conformity is performed through comparison with the prestored information. That is, when a similar part depending on the partial conformity is verified through the comparison, the wearable device 100 knows the distance, a curve, the shape, and the like of the object by geometrically determining the distortion degree. On the contrary, when the 3D data is scanned, since the partial conformity has already been achieved while scanning the object, the shape and the distance of the object may be immediately determined. In such a process, a process in which the location of each joint is determined through the data regarding the vein pattern may be performed or omitted. That is, after the location (for example, a wrist, the joint of the finger, or the like) of each joint is determined from the data regarding the vein pattern, the location and the shape of the entire object (for example, the hand) may be determined, while the location and the shape of the entire object may be immediately determined from the data regarding the vein pattern.

Through the embodiment, the wearable device 100 may distinguish and recognize the body organs and things which are non-body organs. For example, when the user grips the thing with his/her hand, it is very difficult to distinguish the hand of the user and the thing just by 3D scanning. However, since the wearable device 100 combines and processes the blood vessel pattern or the bio pattern with the 3D model according to the aforementioned method, only the body organ may be distinguished and verified and the body organ may be accurately recognized. Through the embodiment, the wearable device 100 allows the user to experience augmented reality (AR) and virtual reality (VR) to be described below.

Meanwhile, when the process in which the coordinate generating unit 120 generates the 3D coordinate of the object is consecutively performed at a short interval, result values depending on the series of processes may represent data to track a motion of the object. In other words, when the process in which the optical signal is transmitted and the reflection optical signal is sensed with respect to the object (a part of the body of the user) is performed repeatedly at the predetermined number of times at the short interval, the coordinate generating unit 120 may generate the 3D coordinate of the object at the predetermined number. The 3D coordinate values are connected to each other, and as a result, the coordinate generating unit 120 recognizes the motion of the object in the space. The motion of the object in the space may be a specific gesture or an operation of triggering an input value prestored in the wearable device 100. Examples of the operation may include a key input operation in which the user presses a predetermined key on a virtual keyboard, a mouse movement operation which the user moves a cursor of a virtual mouse, a mouse click operation in which the user clicks on a button of the virtual mouse, and the like. Detailed processing procedures for the respective operations will be described below.

And, the depth sensor 125 3-dimensionally scans the object and generates 3D scan information. That is, the depth sensor 125 transmits various kinds of signals to the object and senses change of the signals transmitted from the surface of the object or senses signals reflected by the object. The depth sensor 125 may analyze the sensed signals and generate 3D scan information of the object. For example, if the object is a user's hand, the depth sensor 125 may 3-dimensionally sense the user's hand and generate 3D scan information of the external appearance of the user's hand.

The depth sensor 125 serving to 3-dimensionally scan the object may include various kinds of sensors or devices. For example, the depth sensor 125 may include an infrared camera which transmits an infrared signal to an object and senses change of the signal by the surface of the object, a Time of Flight (ToF) camera which transmits an ultrasonic signal or an optical signal to an object and measures a time difference with a signal reflected by the object, a laser transceiver which transmits a laser signal to the object and senses a signal reflected by the object, and a stereo camera which analyzes a difference between values acquired by photographing an object from two positions.

Further, a LIght Detection And Ranging (LIDAR) method in which pulse laser light is radiated into the atmosphere and then a reflective body or a scattering body thereof is used, a speckle interferometry method in which change of a pattern of coherent light reflected by the surface of an object is used, an infrared proximity array (IPA) sensing method using two LEDs, and an RGB camera may be employed to implement the depth sensor 125.

If the depth sensor 125 generates 3D scan information using a patterned optical signal of a specific wavelength, the depth sensor 125 may have the same configuration as the above-described optical signal transmission unit 105. That is, the optical signal transmission unit 105 may use the patterned optical signal both to sense blood vessels and to generate 3D scan information. In this case, the optical signal transmission unit 105 may output the patterned optical signal in addition to output of optical signals having different wavelengths, thus being capable of serving as the depth sensor 125 or serving as only the depth sensor 125. As the patterned optical signal output by the optical signal transmission unit 105 so that the optical signal transmission unit 105 serves as the depth sensor 125, one of the wavelengths of the optical signals to sense blood vessels may be used or an optical signal of another wavelength may be used.

Further, the depth sensor 125 may be operated through two methods, similarly to the description of the optical signal transmission unit 150, and generate scan information. That is, when the depth sensor 125 transmits an optical signal (a patterned optical signal) to the object and generates 3D scan information, the depth sensor 125 may foreknow or may not know the time and frequency band of a received optical signal. In more detail, if the depth sensor 125 foreknows the time and wavelength band (or, the frequency band) of a transmitted optical signal, the depth sensor 125 calculates a time when the corresponding optical signal will be received in advance and generates 3D scan information through the received optical signal of the calculated frequency band at the calculated time. In this case, while the optical signal transmission unit 105 transmits optical signals of specific wavelengths so as to acquire information regarding blood vessels of the object, the depth sensor 125 may transmit an optical signal to generate 3D scan information.

On the other hand, although the depth sensor 125 does not know information regarding the received optical signal, if the depth sensor 125 includes a unit to selectively sense the received optical signal, the depth sensor 125 may generate 3D scan information. That is, the depth sensor 125 may include a filter to detect a specific wavelength band of the optical signal and, in this case, selectively sense the received optical signal.

The depth sensor 125 to 3-dimensionally scan an object is not limited to the embodiment having the above-described elements but may include various other elements. Further, the depth sensor 125 may include a combination of two or more of the above-described elements. When a plurality of components of the depth sensor 125 is used, a stereo technique may be adopted, which scans the object at two or more different locations and analyzes a difference value.

Further, after the depth sensor 125 performs the process of 3-dimensionally scanning the object, the depth sensor 125 may improve precision of 3D scan information using computer vision technique. The computer vision technique is used to improve precision of depth information during a process of interpreting a 2D image and includes a depth-from-focus method, a depth-from-stereo method, a depth-from-shape method, a depth-from-motion method and the like. The depth sensor 125 may precisely generate 3D scan information of the object using the above-described various methods.

Although the above description exemplarily states the case that the object is a part of a user's body, such as a hand, the disclosure is not limited thereto. That is, the object may mean not only a part of a human body but also an article, a space or a structure. For example, if the object is an article, such as a portable terminal, a notebook, or a desk, the depth sensor 125 may 3-dimensionally scan the portable terminal, the notebook, or the desk and generate 3D scan information. Further, if the wearable device 100 is located within a room, the depth sensor 125 may scan a space, 3D objects and walls within the room as the object. Thereby, the depth sensor 125 may recognize a 3D space by the walls of the room and generate 3D scan information of the walls. In this case, the depth sensor 125 may detect the position of the wearable device 100 within the room, i.e., the absolute coordinates of the wearable device 100 within a designated space by comparing a pre-stored 3D objects and values of the 3D scan information.

The bio pattern recognizing unit 130 senses visually verified patterns by scanning the object when the object is a part of the body of the user. Various types of patterns which may be visually distinguished, which include the lines of the palm, a fingerprint, a crease, the blood vessel, the curve, and the like exist on the surface of the body, the bio pattern recognizing unit 130 senses the patterns and uses the sensed patterns as an index by using natural light and indoor light or an optical signal having a specific wavelength. That is, the bio pattern recognizing unit 130 verifies the chroma, the brightness, the color, and the like on the surface of the body to distinguish the patterns. For example, the crease, the lines of the palm, and the like have a characteristic in that the crease, the lines of the palm, and the like are darker and thicker than other parts of the surface of the body and the blood vessel shows a blue color on the surface of the body. The bio pattern recognizing unit 130 visually senses the bodily characteristics and generates a sensed result as pattern information.

The bio pattern recognizing unit 130 may transmit an optical signal having a specific single wavelength for visually verifying a nail, a nail line (nail border), a pore of the skin, the lines of the palm, the fingerprint, the crease, the blood vessel, and the like and unlike this, a multi-spectrum technique using two or more wavelengths may also be used. In the case of the single wavelength, the bio pattern recognizing unit 130 may more easily sense the bodily characteristic by using a blue-color or violet-color visible-ray wavelength area in which the bodily characteristic is well shown.

Further, the bio pattern recognizing unit 130 may recognize the distribution of the bodily characteristic in a broad viewpoint. That is, the bio pattern recognizing unit 130 may not sense only one pattern at a specific location but also sense the distribution of the pattern for a specific area on the surface of the body. For example, the bio pattern recognizing unit 130 may recognize all of a part which is partially dark or bright, a part which is more red or white, a part where the blood vessel is reflected to show a blue color, layouts of the fingerprint and the crease, and the like on the surface of the palm when the object is the palm. Further, the bio pattern recognizing unit 130 may recognize all of the part where the blood vessel is reflected to show the blue color, the crease at the joint location, the curve on the surface of the back of the hand, the nail, and the like when the object is the back of the hand or the arm.

Meanwhile, the information on the pattern generated by the bio pattern recognizing unit 130 may be combined to the 3D model of the body, which is pregenerated by the depth sensor 125. That is, as described in the embodiment in which the blood vessel data is combined to the 3D model, information on the bodily characteristic sensed by the bio pattern recognizing unit 130 may also be used as a means for sensing the 3D coordinate and motions of the components of the body. For example, when the pattern information for the respective components of the body is combined to the 3D model, the wearable device 100 analyzes the sensed bio pattern to distinguish the components of the body by the unit of the joint.

The bio pattern recognizing unit 130 may adopt an RGB camera, an infrared camera, a ToF camera, and the like in order to sense various types of patterns. Besides, the bio pattern recognizing unit 130 may be implemented to include and use various types of sensors applied to the depth sensor 125. The bio pattern recognizing unit 130 recognizes parts where the brightness, the colors, and the chroma are different by photographing or sensing the palm surface of the user by using various types of cameras, sensors, and modules. The recognition result is generated as the pattern information. The bio pattern recognizing unit 130 may also be implemented as a type in which two or more components among the components are combined similarly to the depth sensor 125.

Meanwhile, when the configurations of the optical signal sensor 110 and the bio pattern recognizing unit 130 are implemented to be positioned very adjacent to each other, the information generated by using the wavelength of the visible-ray area in the bio pattern recognizing unit 130 may be used for generating the blood vessel data of the data processor 115. That is, an operation of the bio pattern recognizing unit 130 may be used for determining the bodily characteristic in itself and used even for generating the blood vessel data. In this case, the wavelengths of the visible-ray and near infrared-ray areas may be implemented to be alternatively transmitted and received or when a filter for distinguishing a spectrum of a wide band is used, the wavelengths of the visible-ray and near infrared-ray areas may be simultaneously transmitted and received.

Meanwhile, the bio pattern recognizing unit 130 senses the key input operation, the mouse movement operation, the mouse click operation, and the like of the user as the bodily characteristics of the user are scanned. That is, the bio pattern recognizing unit 130 analyzes the bodily characteristics to sense the key input operation, the mouse movement operation, the mouse click operation, and the like similarly to the coordinate generating unit 120 described above.

As illustrated and described in FIG. 1, the depth sensor 125 and the bio pattern recognizing unit 130 may be implemented as separate configurations, but unlike this, the depth sensor 125 and the bio pattern recognizing unit 130 may be implemented as one configuration. That is, when the depth sensor 125 and the bio pattern recognizing unit 130 are implemented by the infrared camera or the RGB camera, both configurations may not be separate configurations but a single configuration. That is, the infrared camera or the RGB camera may serve as both the depth sensor 125 and the bio pattern recognizing unit 130.

The image processor 135 is connected to the depth sensor 125 and receives and processes the 3D scan information. In more detail, the image processor 135 may generate a 3D image using the 3D scan information received from the depth sensor 125 and generate a 3D model of the object through a 3D rendering process. As one example, if the object is a user's hand, when the depth sensor 125 senses the user's hand, the image processor 135 may generate a 3D model of the hand. As another example, if the object is an article, such as a portable phone, the image processor 135 may generate a 3D model of the portable phone. The 3D model may be expressed in black/white or color.

Further, the image processor 135 may add a pattern of blood vessels to the generated 3D model using the reception data generated by the data processor 115. As described above, the data processor 115 processes the optical signals received by the optical signal sensing unit 110 and generates information regarding blood vessels of the object. The image processor 135 may process the information regarding blood vessels, generate a visually confirmable pattern, and add the generated pattern to the 3D model generated based on the 3D scan information. That is, the image processor 135 may generate a 3D model formed by mapping the pattern regarding blood vessels onto the 3D model representing only the external appearance of the object.

Meanwhile, the wearable device 100 may accumulate and store the information on the blood vessel pattern (alternatively, bio pattern) and use the accumulated and stored information as a database. That is, the wearable device 100 prestores most gestures which the body of the user may take by the unit of the blood vessel data or the bio pattern and compares newly input blood vessel data or bio pattern with prestored candidate images to distinguish which gesture the corresponding gesture is. Such a machine learning method has an advantage in that as the operation is repeated, accuracy of a result value increases.

The image output unit 140 projects an image to the outside. The image output unit 140 may project an image onto an object, such as an article or a part of a human body, and the object is not limited thereto. For example, the image output unit 140 may project an image onto a part of a human body, such as the palm of a hand, the back of a hand or an arm, or project an image onto an article, such as a desk or a wall. The image projected by the image output unit 140 may include all kinds of images, i.e., an arbitrary image, a moving picture, a 3D image (stereoscopic image) and the like. As another example, the image output unit 140 may output the image in a line-of-sight direction in which an eye of the user views. Through the embodiment, the image output unit 140 provides an augmented realty (AR) or virtual reality (VR) service to the user. In other words, the image output unit 140 directly outputs the image to a location which the line of sight of the user faces, and as a result, the user views the image output by the image output unit 140 to overlap with an actual thing. The embodiment will be described in detail in FIG. 8.

An embodiment that outputs the image to the eye by using wearable AR/VR device, head mounted display (HMD), and optical head mounted display (OHMD) concepts will be further described. A wearable AR/VR device, an HMD, and an OHMD mean devices which are mounted on a head of the user to allow the user to experience AR/VR and in such a process, waveguide and virtual retinal display (VRD) technologies may be used.

The concepts are similar in that all of the concepts are mounted on the head of the user. The HMD, the OHMD, the VRD, and the like provide a VR experience to the user in an environment in which external light may not be introduced by the eye or provide an AR experience to the user in an environment in which the external light is introduced into the eye to be combined to a virtual image.

The waveguide is a concept that light is not directly transmitted to the eye of the user (that is, the view of the user is not covered) and the output image is refracted or reflected to combine a virtual image to the line-of-sight direction of the user. According to the implementation method, technologies including a diffractive waveguide, a holographic waveguide, a polarized waveguide, a reflective waveguide, a clear-vu reflective waveguide, a switchable waveguide, and the like may be included in the waveguide technology. The VRD technology is a method that directly transmits LED or a laser to a retina of the user to provide a 3D AR service.

The image output unit 140 may use information determined by the coordinate generating unit 120 during such an image projection process. The coordinate generating unit 120 may generate the 3D coordinate of the object as described above. Meanwhile, since the concept of the 3D coordinate is a relative concept, a case where the wearable device 100 recognizes the 3D coordinate of the object should be simultaneously appreciated even as a case where the wearable device 100 recognizes a spatial location thereof.

In more detail, although the wearable device 100 moves in space, the image output unit 140 may project an output image to a designated position so as to have a designated size using results of the coordinates of the object measured by the coordinate generating unit 120. That is, the wearable device 100 calculates a distance thereof from an external reference point (for example, the object onto which the image is projected) and an angle thereof from the external reference point by measuring and analyzing movement of the position determination unit 135 in a 3D space. Thereafter, the image output unit 140 may control the output angle and position of the image so that the image may be regularly projected, in consideration of the calculated distance and angle.

As another method, the image output unit 140 may consider the information on the bio pattern of the user while projecting the image. That is, the image output unit 140 may transmit the image at a fixed location and a fixed angle based on the bodily characteristic by using the information on the bodily characteristic (the crease, the blood vessel, the curve, the fingerprint, and the like) of the user acquired according to various methods. When the embodiment is combined with the embodiment in which the coordinate generating unit 120 uses the information on the blood vessel, the angle and the location at which the image output unit 140 outputs the image may be more certainly fixed. In other words, each of the locations of the components of the body is calculated through the information on the bio pattern and the blood vessel (vein) pattern information of the finger, the hand, the arm, and the like, and as a result, the image output unit 140 combines the calculated locations with the components of the body to fixedly output the image. The reason is that the wearable device 100 may separately distinguish and recognize the components of the body. For example, when the locations of the finger, the hand, and the arm are respectively distinguished from each other, the image output unit 140 may output the image to the corresponding location of the component of the body so that the user experience the augmented reality (AR) or the virtual reality (VR). As a result, the image is output while the corresponding component of the body is fixed based on the space regardless of the motion of the component of the body of the user. Such a method is a concept which is completely opposite to a method that outputs the image based on the motion of the device in the related art and in the proposed embodiment, even though the device and an image output location move, the image may be output while being fixed to a desired location.

In order to consider the above-described information regarding the bio pattern, the wearable device 100 may detect and manage biometric information, such as user's skin lines, in advance. That is, as described above in Korean Patent Application No. 10-2014-0108341, the wearable device 100 senses user's skin lines through a finger recognition unit including an infrared camera, an RGB camera or a ToF camera. Information regarding the sensed skin lines is processed as information regarding a skin line pattern and is stored and managed in the wearable device 100. Thereafter, the wearable device 100 may sense user's skin lines during a process of projecting an image and analyze the sensed skin lines through comparison between the sensed skin lines and the stored information regarding a skin line pattern. The wearable device 100 may detect the position and movement of a part of a user's body through such a process and output an image to a fixed position at a fixed angle, as described above.

Although the above description states that the optical signal transmission unit 105 and the image output unit 140 are separately provided, two elements may be combined into one unit. That is, the optical signal transmission unit 105 may not only transmit optical signals of various wavelengths but also transmit an image output from the wearable device 100. Such processes may be alternately carried out. That is, the optical signal transmission unit 105 configured to serve as the image output unit 140 may output an image periodically or aperiodically between alternate output of optical signals of different wavelengths. If optical signals to sense blood vessels are output during output of an image, the image may be applied to the above-described process of selectively detecting an optical signal of a specific wavelength. That is, since the image processor outputs an image of a visible light wavelength visually recognizable by a user, the optical signal of the visible light wavelength output by the image processor is used as one of optical signals to sense blood vessels. Thereby, only if the optical signal transmission unit 105 further transmits only an optical signal of an infrared light wavelength, the optical signal transmission unit 105 may acquire the same/similar effects as/to transmission of two optical signals of different wavelengths.

That is, the optical signal transmission unit 105 may sequentially repeat output of a first optical signal, output of a second optical signal and output of an image and output of the optical signals may be carried out for a shorter time than output of the image. In this case, the user may not sufficiently visually recognize the optical signals output for a short time but may confirm only the image.

Configuration of the optical signal transmission unit 105 and the depth sensor 125 into one unit has been described above. That is, if the optical signal transmission unit 105 performs the function of the depth sensor 125 and the function of the image output unit 140, the three elements may be combined into one unit. In this embodiment, the optical signal transmission unit 105 may transmit a patterned optical signal in addition to transmission of optical signals during output of the image, thus being capable of performing the depth sensor 125.

The gyroscope sensor 145 measures an angular velocity and thus senses the tilt of the wearable device 100. Kinds and functions of gyroscope sensors will be apparent to those skilled in the art and a detailed description thereof will thus be omitted. The acceleration sensor 150 may measure change of a velocity and thus sense the acceleration and tilt of the wearable device 100. Also, kinds and functions of gyroscope sensors will be apparent to those skilled in the art and a detailed description thereof will thus be omitted.

The gyroscope sensor 145 and the acceleration sensor 150 measure movement of the wearable device 100 in a 3D space. That is, the gyroscope sensor 145 and the acceleration sensor 150 measure a movement direction, a movement speed, and a movement slope of the wearable device 100 in the 3D space to measure the spatial motion of the wearable device 100 itself. Accordingly, the wearable device 100 may more accurately measure the 3D coordinate of the wearable device 100 by using measurement values of the gyroscope sensor 145 and the acceleration sensor 150 together with a calculation result value of the coordinate generating unit 120.

Meanwhile, the wearable device 100 measures the spatial motion through the gyroscope sensor 145 and the acceleration sensor 150 to sense the mouse input/movement operation. The mouse input/movement operation means an input in which the user operates the cursor of the mouse by moving the wearable device 100 in the space while wearing the wearable device 100. The wearable device 100 senses and calculates the motion in the space of the wearable device 100 by using the measurement values sensed by the gyroscope sensor 145 and the acceleration sensor 150 and the coordinate value of the coordinate generating unit 120 to generate a predetermined value of the cursor which matches the mouse input/movement operation. The predetermined value may be expressed as movement of the mouse cursor in the image output by the image output unit 140.

That is, the wearable device 100 may serve as a "spatial mouse" which transmits the cursor value to the outside and serves as an input device. Further, the wearable device 100 may generate a 3D model of a human body or an external object using the above-described depth sensor 125 and thus serve as a spatial mouse for the human body or the external object.

Further, a mouse click motion in connection with the mouse movement operation will be described. A mouse click motion means input in which, while a user wearing the wearable device 100 performs the mouse movement operation, the user clicks a left or right button of the mouse by contact of two or more fingers. For example, the wearable device 100 may recognize a case that the thumb and forefinger of a user's hand contact each other as a mouse click motion of the left button of the mouse and recognize a case that the middle finger and thumb of the user's hand contact each other as a mouse click motion of the right button of the mouse. A mouse click value corresponding to the click motion may be generated and transmitted to an external device or the server.

The feedback unit 155 is a unit to transmit tactile feedback to a user using various units. In various cases, the tactile feedback may be generated and transmitted to the user. For example, if the wearable device 100 is located at specific coordinates in a space or passes through the corresponding coordinates, and if a signal indicating transmission of the tactile feedback to the user is received from a content reproduced in an external device connected to the wearable device 100, the tactile feedback may be provided to the user.

The feedback unit 155 may transmit the tactile feedback to the user through various units. For example, the feedback unit 155 may include a vibration module to transmit a vibration signal to a user or include a pressure module so that a user wearing the wearable device 100 may feel pressure. Further, the feedback unit 155 may provide the tactile feedback to the user through a shear stress module or transmit microcurrent, which does not influence a user's body, through a current module.

The communication unit 160 executes data communication and transmission and reception of signals with the outside. For example, the communication unit 160 may be connected to an external network wirelessly, communicate with an external device or the server, and include one or more communication modules for communication.

The communication unit 160 may include modules to execute a communication function, such as wireless LAN, Wi-Fi, Bluetooth, ZigBee, Wi-Fi Direct (WFD), Ultra Wide-Band (UWB), Infrared Data Association (IrDA), Bluetooth Low Energy, and Near Field Communication (NFC) modules, as modules for short range communication.

The communication unit 160 may transmit an input result value generated by the coordinate generating unit 120, the cursor, and the like (for example, the 3D coordinate value, a measurement value corresponding to the click key input operation, a measurement value corresponding to the mouse movement operation, a measurement value corresponding to the mouse click operation, and the like) to the outside by using the communication module. Further, the communication unit 160 may receive 3D positional information from an external device through the communication modules.

The storage unit 165 may store data and information input to and output from the wearable device 100. For example, the storage unit 165 may store the measured values generated by the coordinate generating unit 120. Further, the storage unit 165 may store various kinds of program data or algorithm data executable by the wearable device 100.

The storage unit 165 may include at least one storage medium of a flash memory type, a multimedia card micro type, a card type memory (for example, an SD or XD memory), a Random Access Memory (RAM), a Static Random Access Memory (SRAM), a Read-Only Memory (ROM), an Electrically Erasable Programmable Read-Only Memory (EEPROM) and a Programmable Read-Only Memory (PROM). Further, the wearable device 100 may use web storage or a cloud server which performs the storage function of the storage unit 165 over the Internet.

The power supply unit 170 supplies power to drive the wearable device 100. The power supply unit 170 may include various kinds of power supply units, such as a Li-ion battery, a Li-polymer battery and the like, and the wearable device 100 may include a plurality of power supply units 200. The power supply unit 170 may be connected to other elements of the wearable device 100 by wire so as to supply power to the wearable device 100 and be charged by external power received wirelessly through wireless power transmission. Further, the power supply unit 170 may include a flexible battery which may be bent or spread to a designated degree or more.

The controller 175 is connected to the above-described elements and controls the overall operation of the wearable device 100. For example, when the optical signal transmission unit 105 transmits optical signals and the optical signal sensing unit 110 senses reflected optical signals, the controller 15 may control the data processor 115 so as to process the reflected optical signals and generate reception data. Further, the controller 175 may control the coordinate generating unit 120 to generate the 3D coordinate value based on the reception data. Furthermore, the controller 175 may control the image output unit 140 to output the image to a fixed location with a fixed size or control the image processor 135 to generate the 3D model. That is, the controller 175 may control various functions allowing the wearable device 100 to be operated as an input unit or an output unit according to user's motions.

Hereinafter, an embodiment in which the wearable device 100 is operated according to movement of a user's body will be described. Hereinafter, if not particularly described, an embodiment is illustrated, in which the illustrated wearable device is implemented in a form of a neck wear mounted on the neck of the user. The wearable device 100 implemented in the neck wear form may be implemented to be mounted on the neck of the user and furthermore, the wearable device 100 may be implemented in a form of a necklace worn on the neck of the user through a separate connection means (for example, a strap or a band). The examples are just an example and the wearable device 100 may be implemented in various forms including a spectacles form, a cap form, a helmet form, a head mounted display form, a glove form, a bracelet form, a clip form, a ring form, and the like in addition to the neck wear form. That is, an outer shape of the wearable device 100 is not limited to a specific embodiment.

Further, the wearable device 100 may be implemented as a separated type into two or more pieces. That is, the elements shown in FIG. 1 may be included in any one piece or two or more pieces of the wearable device 100 and the two or more pieces of the wearable device 100 may transmit and receive data by interworking with each other. That is, the wearable device 100 may include some or all of the elements shown in FIG. 1 and, if the wearable device 100 includes some of the elements, the wearable device 100 may be operated in cooperation with another wearable device 100 including other elements.

Figure 2:
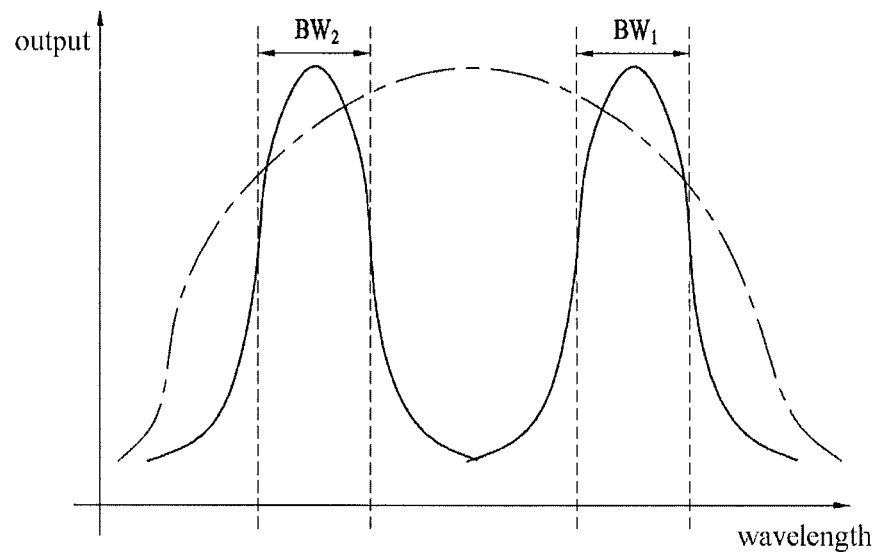
FIG. 2 is a view illustrating an operating process of the wearable device in accordance with one embodiment of the present invention.

FIG. 2 is a view illustrating an operating process of the wearable device in accordance with one embodiment of the present invention. A graph shown in FIG. 2 represents outputs of optical signals transmitted by the wearable device according to wavelength bands. In FIG. 2, a horizontal axis represents the wavelength and a vertical axis represents the output of the optical signal.

As described above, the wearable device may generate optical signals of various wavelengths and transmit the generated optical signals. Hereinafter, a process of transmitting two optical signals of different wavelengths through the wearable device in accordance with the embodiment of the present invention will be described. For convenience of description, the wavelengths of the two optical signals may be respectively referred to as first and second wavelengths, the first wavelength may mean a wavelength within a first frequency band ($BW_1$), and the second wavelength may mean a wavelength within a second frequency band ($BW_2$). As one example, the first frequency band ($BW_1$) may be the frequency band of near infrared light and the second frequency band ($BW_2$) may be the frequency band of visible light. That is, the wearable device may generate and transmit the first optical signal having the first wavelength of near infrared light and the second optical signal having the second wavelength of visible light. As another example, the first frequency band ($BW_1$) and the second frequency band ($BW_2$) may be frequency bands of near infrared light. That is, the wearable device may generate and transmit two optical signals having near infrared light wavelengths.

In order to output the first optical signal and the second optical signal, the wearable device may generate an optical signal having the wavelength of a continuous spectrum or generate optical signals having respective wavelengths or wavelength bands. In more detail, the wearable device may respectively generate a first optical signal and a second optical signal having different wavelengths, as shown by a solid line of FIG. 2. On the other hand, the wearable device may generate an optical signal having the wavelength of a relatively broad continuous spectrum, as shown by a dotted line of FIG. 2, and output optical signals having a first wavelength and a second wavelength using a designated filter (for example, a band pass filter).

In the former case, the wearable device may include only one optical signal transmission unit to generate the two optical signals or include two or more optical signal transmission units to respectively generate the two optical signals having different wavelengths. In the latter case, the wearable device may include a single optical signal transmission unit or include two or more optical signal transmission units.

Figure 3:
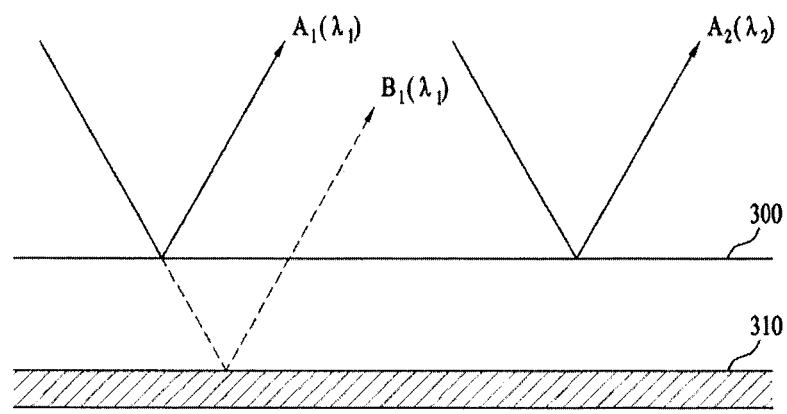
FIG. 3 is a view illustrating an operating process of the wearable device in accordance with one embodiment of the present invention.

FIG. 3 is a view illustrating an operating process of the wearable device in accordance with one embodiment of the present invention. FIG. 3 illustrates a process in which, if the object is a human body, the wearable device transmits optical signals and senses reflected optical signals. In FIG. 3, the object 300, which is a human body, may be, for example, the skin of a hand, and a shaded part in the object 300 may be a blood vessel 310 within the human body.

First, as described in FIG. 2, the wearable device generates and transmits two or more optical signals having different wavelengths. In the embodiment of FIG. 3, $A_1$ and $B1$ having a wavelength $\lambda_1$ represent a first optical signal transmitted by the wearable device, and $A_2$ having a wavelength $\lambda_2$ represents a second optical signal transmitted by the wearable device. The wearable device generates two optical signals of different wavelengths and transmits the optical signals to the skin of a human body. In the embodiment of FIG. 3, the first optical signal has the wavelength of a near infrared band and the second optical signal has the wavelength of a visible band.

Skin tissues, blood vessels and the like are present within the human body and consist of different components. Particularly, blood vessels include red corpuscles including hemoglobin and are thus red. Hemoglobin is divided into oxyhemoglobin and deoxyhemoglobin. A large amount of oxyhemoglobin is present in arteries and oxyhemoglobin transmits oxygen to tissues of the human body. A large amount of deoxyhemoglobin is present in veins after transmission of oxygen to the tissues of the human body. That is, arteries and veins have different physical properties due to different kinds of hemoglobin located in arteries and veins. Particularly, oxyhemoglobin/deoxyhemoglobin included in veins have different absorption rates according to change of the wavelength of light. Since veins including oxyhemoglobin/deoxyhemoglobin has a higher absorption rate to a near infrared range wavelength (about 700 to 900 nm) than other surrounding tissues, there is a great difference between amounts of an optical signal of a near infrared range scattered/reflected by veins and other tissues. Such a difference is confirmed as a great brightness difference if an image is generated using the wavelength of the near infrared range. Oxyhemoglobin and deoxyhemoglobin in blood vessels have a high absorption rate to an optical signal of a near infrared band but tissues around blood vessels scatter such an optical signal. Therefore, when an optical signal of a near infrared band reflected by the skin is received, a brightness difference due to a difference in absorption rates between blood vessels and surrounding tissues is confirmed and such a brightness difference may be processed as information of a vein pattern.

The wearable device may sense blood vessels of the human body using a physical property difference of these blood vessels (veins) and other surrounding tissues. That is, the first optical signal $A_1$, $B_1$ and the second optical signal $A_2$ have different wavelengths, a part $A_1$ of the first optical signal $A_1$, $B_1$ is reflected/scattered by the skin of the object 300, and the remainder $B_1$ passes through the skin of the object and is reflected/scattered by the blood vessel 310 and tissue in the object. The latter $B_1$ reaches the blood vessel 310 and is scattered/reflected by deoxyhemoglobin of the vein. The second optical signal $A_2$ is reflected/scattered by the skin of the object 300 similarly to the part $A_1$ of the first optical signal $A_1$, $B_1$. That is, the first optical signal $A_1$, $B_1$ is an optical signal of a wavelength transmitted by the object 300, passes through layers of the skin and is reflected/scattered/absorbed by the respective layers of the skin. The second optical signal $A_2$ is scarcely transmitted by the object, scattered/reflected by the outer surface of the skin, and has similar features to the part $A_1$ of the first optical signal $A_1$, $B_1$.

The wearable device transmits the first optical signal $A_1$, $B_1$ and the second optical signal $A_2$ to the object and receives optical signals reflected by the object. Such reflected optical signals include a reflected optical signal $A_1+B_1$ acquired upon reflection of the first optical signal $A_1$, $B_1$ by the skin, the internal body organ, and the vein and a reflected optical signal $A_2$ acquired upon reflection of the second optical signal $A_2$. For convenience of description, the reflected optical signal $A_1+B_1$ of the first optical signal $A_1$, $B_1$ is referred to as a first reflected optical signal and the reflected optical signal $A_2$ of the second optical signal $A_2$ is referred to as a second reflected optical signal.

The wearable device generates reception data through processing of the first reflected optical signal and such reception data includes all information regarding the skin and blood vessels of the object.

Thereafter, the wearable device retransmits the second optical signal $A_2$ having a wavelength differing from the wavelength of the first optical signal $A_1$, $B_1$ to the object. That is, the newly transmitted second optical signal $A_2$ has a wavelength differing from the wavelength of the first optical signal $A_1$, $B_1$ transmitted by the wearable device but similarly includes information regarding the surface of the skin, i.e., the information acquired by the part $A_1$ of the first optical signal $A_1$, $B_1$. That is, the second optical signal $A_2$ is reflected by the skin of the object and received by the wearable device, and the reflected optical signal $A_2$ of the second optical signal $A_2$ similarly includes a part of the information included in the first reflected optical signal $A_1+B_1$.

The wearable device generates reception data through processing of the second reflected optical signal $A_2$, and such reception data includes only information regarding the skin differently from the reception data generated through processing of the first reflected optical signal $A_1+B_1$.

The wearable device compares the reception data generated based on the first reflected optical signal $A_1+B_1$ and the reception data generated based on the second reflected optical signal $A_2$ with each other. Such a comparison process includes subtraction of the data of the second reflected optical signal $A_2$ from the data of the first reflected optical signal $A_1+B_1$ by comparing the two reception data with each other. That is, the wearable device may acquire only information regarding blood vessels 310 within the object from the first reflected optical signal $A_1+B_1$ by removing influence of the second reflected optical signal $A_2$ from the data of the first reflected optical signal $A_1+B_1$. That is, the wearable device may remove information regarding the skin from the first reflected optical signal $A_1+B_1$ and acquire only information regarding blood vessels from the part $B_1$ of the first reflected optical signal $A_1+B_1$, data acquired through subtraction between the data acquired from the two reflected optical signals may become blood vessel data.

Although this will be described later in detail, the wearable device senses a user's key input motion and generates an input value using information regarding blood vessels included in the blood vessel data. Thereby, the wearable device needs to be operated so as to precisely extract only information regarding blood vessels. The wearable device may effectively acquire only information regarding blood vessels by transmitting optical signals of different wavelengths and calculating a difference therebetween, as described above.

The above description states that the wearable device respectively receives the first reflected optical signal and the second reflected optical signal. Hereinafter, how the wearable device separately senses the two reflected optical signals of different wavelengths will be described. Three methods through which the wearable device receives the first reflected optical signal of the first wavelength and the second reflected optical signal of the second wavelength will be described.

First, the wearable device may separately sense reflected optical signals according to wavelengths. That is, since the wavelengths of the first reflected optical signal and the second reflected optical signal are different, the wearable device may simultaneously receive the two reflected optical signals and then individually process the respective reflected optical signals. That is, although the wearable device simultaneously transmits two optical signals of different wavelengths and simultaneously receives two reflected optical signals, the wearable device may separately process the reflected optical signals according to wavelengths. For example, the wearable device may include photo detectors to separately sense optical signals according to wavelengths.

In the first method, the wearable device may selectively sense the reflected optical signals of different wavelengths. Thereby, although the wearable device transmits optical signals through various manners, i.e., alternately transmits the first optical signal of the first wavelength and the second optical signal of the second wavelength, simultaneously transmits the two optical signals, or periodically or aperiodically transmits one optical signal while continuously transmitting the other optical signal, the wearable device may separately sense reflected optical signals.

Second, the wearable device may separately sense reflected optical signals according to time domains or frequency domains. That is, the wearable device may transmit optical signals of different wavelengths with a time difference or transmit optical signals of different wavelengths at different intensities. Differently from the first method, although the reflected optical signals are not separated from each other according to wavelengths, the wearable device foreknows the transmission times of the optical signals of designated wavelengths and may thus estimate which reflected optical signals correspond to the optical signals.

In the second method, the wearable device may alternately transmit the first optical signal of the first wavelength and the second optical signal of the second wavelength. In this case, the wearable device foreknows which reflected optical signals correspond to the optical signals and thus, a burden to separate the reflected optical signals according to wavelengths may be reduced. In this method, the wearable device may alternately transmit the two optical signals or periodically or aperiodically transmit one optical signal while continuously transmitting the other optical signal.

Third, there is a case that optical signals are transmitted at different intensities. The wearable device may transmit different optical signals at different output intensities. This method may be combined with the above-described first method and second method. In this method, the wearable device senses a relatively large intensity difference between the reflected optical signals and thus more effectively detects the reflected optical signals according to time domains or frequency domains.

The above description states the embodiment in which the wearable device transmits the first optical signal and the second optical signal and analyzes the reflected optical signals. However, the optical signals generated and received by the wearable device may be influenced by indoor light and natural light in surrounding environments where the wearable device is operated. For example, if the wearable device generates a second optical signal of a visible light wavelength and transmits the second optical signal to an object, a reflected optical signal of the second optical signal may be mixed with an optical signal generated upon reflection of sunlight by the object and thus, noise may be generated. Therefore, a process for removing such noise may be required.

There are various methods for removing the influence of external light. First, the wearable device may be operated so as to exclude external factors, such as natural light, indoor light, light due to a beam projector and the like. That is, the wearable device may recognize light, sensed by the optical signal sensing unit prior to transmission of optical signals from the optical signal transmission unit, as external light. Thereafter, the wearable device may remove influence of the external light from reflected optical signals sensed after transmission of the optical signals, thus acquiring only reflected optical signals of the optical signals transmitted from the wearable device.

Second, the wearable device may use external light instead of removal of the influence of external light. That is, if the wearable device uses an optical signal of a near infrared wavelength as the first optical signal and an optical signal of a visible wavelength as the second optical signal, the wearable device may selectively receive external light instead of direct generation and transmission of the first optical signal and the second optical signal. In more detail, the first optical signal and the second optical signal which the wearable device desires to generate may be generated by external light. In this case, the wearable device may filter a reflected optical signal generated upon reflection of the external light by the object and thus selectively receive reflected optical signals of designated wavelengths. Thereby, although the wearable device does not directly generate optical signals, the wearable device may acquire the same or similar effect as or to direct generation of the optical signals using external light. However, if external light is used, optical signals of desired wavelengths may not be sufficiently received and thus, the wearable device may analyze the external light and additionally generate and transmit only an optical signal of a necessary wavelength to supplement the external light.

Accordingly, in order to receive reflected optical signals of specific wavelengths, the wearable device may directly generate optical signals and transmit the optical signals to an object so as to acquire a desired result, or selectively receive external light so as to acquire the same result.

In the above description, the terms first optical signal, second optical signal, first reflected optical signal, second reflected optical signal and the like are used. However, it will be understood that the terms "first", "second", etc. may be used only to discriminate one element from other elements, and the scope of the present invention is not limited by these terms.

The above-described first optical signal and second signal may be a signal of a near infrared range and a signal of a visible range. However, the disclosure is not limited thereto and the first optical signal and the second optical signal may be optical signals of a near infrared range or optical signals of an infrared range. That is, only if the wavelength bands of the two optical signals are different, the wearable device may transmit the two optical signals, receive reflected optical signals and thus acquire information regarding blood vessels. Since skins, blood vessels and surrounding tissues have different absorption/scattering/reflection rates according to wavelengths of optical signals, different first reflected optical signal and second reflected optical signal of a near infrared range or an infrared range include different pieces of biometric information. That is, the wearable device transmits two or more optical signals and thus acquires information regarding blood vessels but wavelength bands or kinds of the optical signals are not limited. Therefore, although hereinabove and hereinafter a near infrared range and a visible range are exemplarily described, it may be understood that optical signals having different wavelength bands are used.

In accordance with another embodiment, the wearable device may acquire information regarding blood vessels using only one optical signal not two optical signals. That is, as described above, blood vessels and surrounding tissues have different absorption rates and scattering rates to an optical signal of a near infrared band (700 nm-900 nm). The reason for this is that skin tissue layers have different reflection rates according to variation of the spectrum and wavelength of an optical signal. The wearable device may confirm a brightness difference between blood vessels and surrounding tissues through comparison/combination/analysis of such information and detect a pattern of the blood vessels. Of course, a method in which the wearable device transmit and receives three or more optical signals may be employed. During a process of using two or more optical signals, the optical signals may have different wavelengths, different spectrums, different transmission times (points of time), different reception times (points of time), different frequencies or different polarization states.

Overall, the wearable device may transmit a plurality of optical signals having different wavelengths in a visible range and an infrared range, receive reflected optical signals and execute comparison/analysis/combination of the optical signals according to wavelengths, thus acquiring image data of blood vessels and surrounding tissues.

Otherwise, the wearable device may acquire image data of blood vessels and surrounding tissues by transmitting and receiving only one optical signal in a single near infrared range, thus recognizing a pattern of the blood vessels. Consequently, the wearable device may acquire information regarding blood vessels by transmitting and receiving one or more optical signals.

In accordance with an embodiment in which two methods are combined, the wearable device may transmit and receive two or more optical signals during a process of initially acquiring blood vessel data and then transmit and receive one optical signal during a process of sensing a user's key input motion. On the other hand, the wearable device may transmit and receive only one optical signal during a process of initially acquiring blood vessel data and then transmit and receive two or more optical signals during a process of sensing user's movement.

Figure 4:
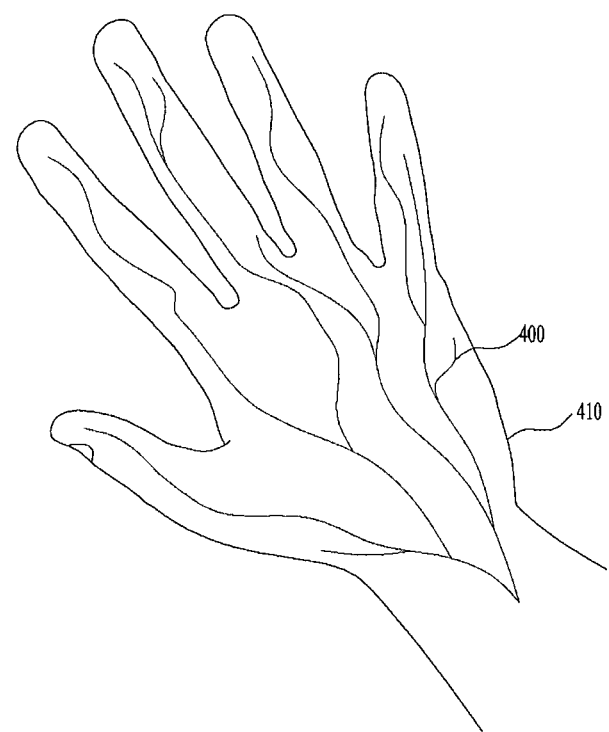
FIG. 4 is a view illustrating an operating process of the wearable device in accordance with one embodiment of the present invention.

FIG. 4 is a view illustrating an operating process of the wearable device in accordance with one embodiment of the present invention. In FIG. 4, various embodiments for the input value of the wearable device will be described.

As described above, the wearable device senses the object to measure the 3D coordinate value of the object. In such a process, the components including the optical signal transmission unit, the optical signal sensor, the depth sensor, the bio pattern recognizing unit, and the like described in FIG. 1 are used, and all components need not be simultaneously used for the operation of the wearable device. Hereinafter, in some cases, a process in which the components included in the wearable device measure the 3D coordinate value of the object will be described. Further, the since the optical signal transmission unit and the optical signal sensor operate in connection with each other, the process is described by assuming that the optical signal transmission unit and the optical signal sensor are implemented with the same number.

First, a case where the wearable device includes one optical signal transmission unit/optical signal sensor and one depth sensor or a case where the wearable device includes one bio pattern recognizing unit and one depth sensor may be considered. In the embodiment, data regarding the object sensed by the optical signal transmission unit/optical signal sensor or the bio pattern recognizing unit is analyzed together with the 3D model of the object sensed by the depth sensor and the wearable device generates the 3D coordinate.

As another example, the wearable device may include all of one optical signal transmission unit/optical signal sensor, one bio pattern recognizing unit, and one depth sensor. In this case, information regarding the object measured by the optical signal transmission unit/optical signal sensor and information regarding the object measured by the bio pattern recognizing unit may have a relationship in which both information complements each other. For example, when the distribution of the vein is minute in the finger and it is thus difficult to generate the accurate 3D coordinate only by a measurement value of the optical signal transmission unit/optical signal sensor, the information regarding the object sensed by the bio pattern recognizing unit may enhance accuracy in the process of generating the 3D coordinate (alternatively, and vice versa).

Furthermore, the wearable device may be configured to include only two or more optical signal transmission unit/optical signal sensor sets. In this case, the respective optical signal transmission unit/optical signal sensor sets independently scan the object and the blood vessel data is also separately generated. Hereinafter, a method that measures different data regarding the object through two or more same means as described in the embodiment is referred to as 'stereo sensing'. The wearable device analyzes relative locations of two different blood vessel data to acquire the spatial 3D coordinate of the object. On the contrary, the wearable device may include two or more bio pattern recognizing units and similarly even in the example, results of the stereo sensing by two or more respective bio pattern recognizing units are separately analyzed, and as a result, the 3D coordinate of the object is generated.

Furthermore, the wearable device may include the depth sensor in addition to two or more optical signal transmission units/optical signal sensors (alternatively, two or more bio pattern recognizing units). In this case, information regarding the 3D model of the object sensed by the depth sensor serves to increase the accuracy in measurement while determining the 3D coordinate of the object.

According to yet another embodiment, the wearable device may include two or more optical signal transmission units/optical signal sensors and one bio pattern recognizing unit. In this case, when two or more blood vessel data are generated as a result of performing the stereo sensing through the optical signal transmission units/optical signal sensors and in addition, the wearable device generates the 3D space coordinate by using even the information on the object sensed through the bio pattern recognizing unit. The wearable device may use or not use the depth sensor. When the wearable device uses the depth sensor, it is advantageous in terms of the accuracy in result value, but it may be disadvantageous in terms of calculation complexity, such that a trade-off occurs. On the contrary, the wearable device may include two or more bio pattern recognizing units and one optical signal transmission unit/optical signal sensor and the wearable device operates similarly to the aforementioned embodiment.

When the embodiment is developed, the wearable device may be configured to include two or more optical signal transmission units/optical signal sensors and two or more bio pattern recognizing units. The wearable device may use or not use the depth sensor as described above.

FIG. 4 is described in association with various embodiments described above. In FIG. 4, the wearable device is mounted on the body of the user to sense the hand of the user which is an object 410 and acquire information on a blood vessel 400 in the object 410. That is, the wearable device is mounted on a part of the body of the user or the thing to transmit the optical signal to the object 410 and receives the reflection optical signal reflected outside or inside the object 410 to acquire information on the object 410 and the information on the blood vessel 400. The wearable device may include two or more components for transmitting/receiving the optical signal as described above.

Meanwhile, the wearable device may sense a bio characteristic (alternatively, pattern) visually verified on the surface of the object 410 by using the RGB camera, the infrared camera, the ToF camera, and the like. That is, the wearable device senses the color, the chroma, the brightness, the form, and the like of the bio characteristic to acquire information of different types from the data regarding the blood vessel 400.

Subsequently, the wearable device analyzes at least one of two types of information to generate the 3D coordinate for the object 400. Such a process may be appreciated as a process that analyzes one type of data measured through the stereo sensing or a process that analyzes two types of different data.

Figure 5:
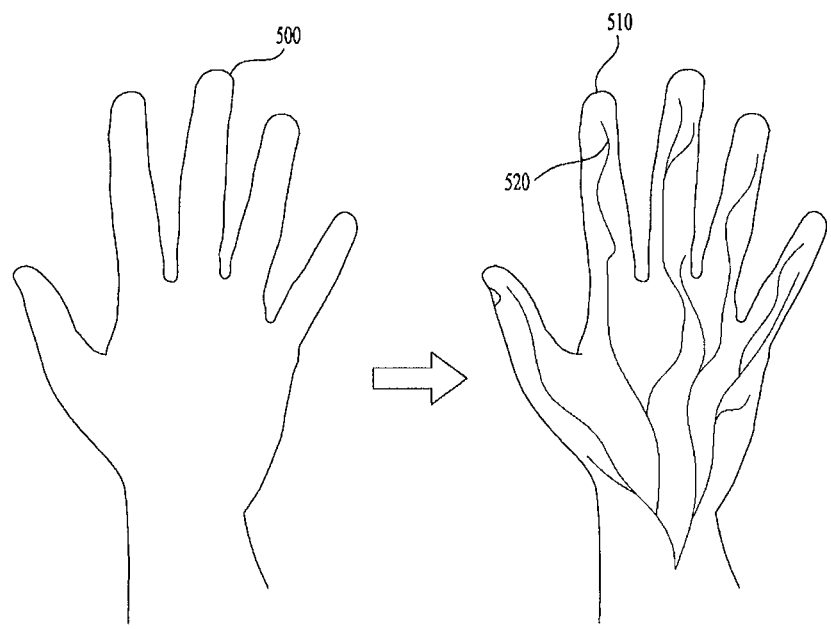
FIG. 5 is a view illustrating an operating process of the wearable device in accordance with one embodiment of the present invention.

FIG. 5 is a view illustrating an operating process of the wearable device in accordance with one embodiment of the present invention. FIG. 5 illustrates a process of generating a 3D model of a user's hand through the wearable device. In FIG. 5, an embodiment in which the wearable device uses the depth sensor is described in addition to the embodiment described in FIG. 4.

First, the left portion of FIG. 5 will be described. The depth sensor of the wearable device 3-dimensionally senses a user's hand and generates 3D scan information. The user allows the wearable device to perform a 3D scan process while rotating the hand clockwise or counterclockwise so as for the wearable device to accurately scan the object in 3D.

The depth sensor generates 3D scan information of the user's hand and transmits the corresponding information to the image processor. The image processor generates a 3D model 500 of the user's left hand by analyzing and processing the 3D scan information. The 3D model 500 may be a 3D image and be generated through a 3D rendering process.

The 3D model 500 generated using a result of scanning by the depth sensor, i.e., the 3D scan information, may not sufficiently include information regarding blood vessels required by the wearable device. That is, blood vessels on the surface of a human body are visible dimly and are not clear enough to be sensed by the wearable device so as to generate an input value. That is, the depth sensor may precisely measure the external appearance of the user's hand but may not sense detailed features, such as the distribution and arrangement of blood vessels.

Thus, a process of adding a pattern to the 3D model 500 is performed, as shown in the right portion of FIG. 5. The wearable device acquires information of blood vessels of the object using the optical signal transmission unit and the optical signal sensing unit, as described above with reference to FIGS. 2 and 3, and a pattern 520 of the blood vessels is generated using the acquired information.

A series of processes of sensing blood vessels and generating pattern information through the wearable device may be carried out simultaneously with or separately from the process of generating 3D scan information through the depth sensor. That is, while the depth sensor 3-dimensionally recognizes a user's hand and generates 3D scan information, the optical signal sensing unit may sense the blood vessels and the data processor may generate pattern information. In this case, both the 3D scan information and the pattern information regarding blood vessels are transmitted to the image processor and the image processor sequentially processes the two pieces of information and generates a 3D model. In such an embodiment, a pattern-added 3D model 510 having the pattern 520 may be generated through one scan process.

Differently, when the depth sensor scans a hand and generates 3D scan information and the image processor generates a 3D model using the 3D scan information, a process of generating pattern information through the optical signal sensing unit and the data processor may be additionally performed. In this case, the process of scanning an object, i.e., a hand, through the wearable device needs to be carried out twice. That is, in the former case, both 3D scan information and pattern information are generated by one scan process but, in the latter case, 3D scan information may be generated through the first scanning process and pattern information may be generated through the second scanning process. In the latter case, the image processor generates a 3D model in advance and then processes received pattern information.

The pattern information generated by the data processor is transmitted to the image processor and a process of mapping the pattern 520 onto the 3D model 500 is performed. That is, the image processor may generate the pattern-added 3D model 510 by executing the process of mapping the pattern 520 onto the 3D model 500 generated by the 3D scan information. The pattern 520 includes information regarding blood vessels, and blood vessels (for example, veins) have different depths and thicknesses according to parts of a human body (e.g., back of a hand, palm of a hand, fingers, etc.) and may thus be considered as 3D stereoscopic structures. Therefore, the pattern 520 of the blood vessels mapped onto the 3D model 500 may have 3D information (depth, thickness, direction and the like) on the surface of the skin and under the surface of the skin.

Similarly to the aforementioned process, the bodily characteristics by the bio pattern recognizing unit may be added to a 3D model 500 as the pattern. That is, the wearable device may add the bodily characteristics generated when the bio pattern recognizing unit senses the color, the chroma, the brightness, the form, and the like of the object to the pregenerated 3D model 500.

Hereinabove, the embodiment has been described, in which the wearable device pregenerates the 3D model and adds to the pregenerated 3D model the data generated by the optical signal transmission unit/optical signal sensor or the bio pattern recognizing unit. However, the embodiment is just an example and the 3D coordinate of the object may be generated without omitting the 3D model using the depth sensor as described in FIG. 4 above. That is, the 3D model is used for enhancing the accuracy of the result of measuring the spatial location of the object while the wearable device generates the 3D coordinate of the object. Meanwhile, the wearable device may measure the bio pattern, the vein pattern, or the 3D coordinate of the object with sufficient accuracy by using the stereo sensing method or two or more different types of object sensing means. In this case, the process in which the wearable device pregenerates the 3D model may be omitted.

Figure 6:
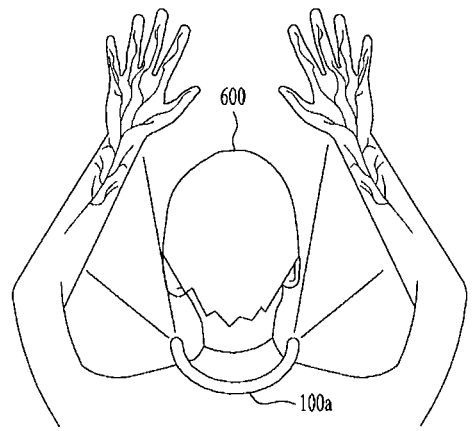
FIG. 6 is a view illustrating an operating process of the wearable device in accordance with one embodiment of the present invention.
Figure 6:
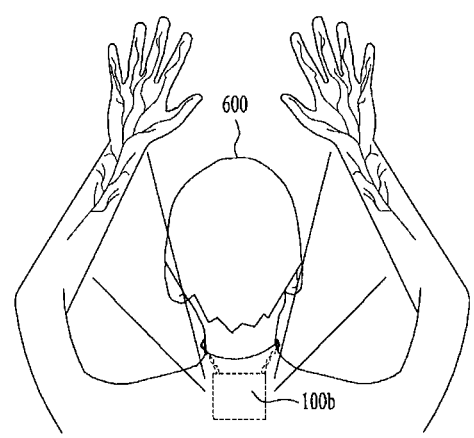

FIG. 6 is a view illustrating an embodiment of an operating process of the wearable device implemented in a neck wear form and a necklace form. FIG. 6(*a*) illustrates a neck wear type wearable device 100*a* mounted on the neck of a user 600 and FIG. 6(*b*) illustrates a necklace type wearable device 100*b* mounted on the neck of the user 600 in association with a predetermined connection means.

In both cases of FIGS. 6(*a*) and 6(*b*) illustrated, the wearable devices 100*a* and 100*b* may scan both a left hand and a right hand of the user 600. This means that the wearable devices 100*a* and 100*b* include two or more optical signal transmission units/optical signal sensor sets or two or more bio pattern recognizing units. Alternatively, the wearable devices 100*a* and 100*b* may include one optical signal transmission unit/optical signal sensor set or one bio pattern recognizing unit, but measure the left hand and the right hand as the object while changing the object measured by the corresponding component at a predetermined time interval.

Figure 7:
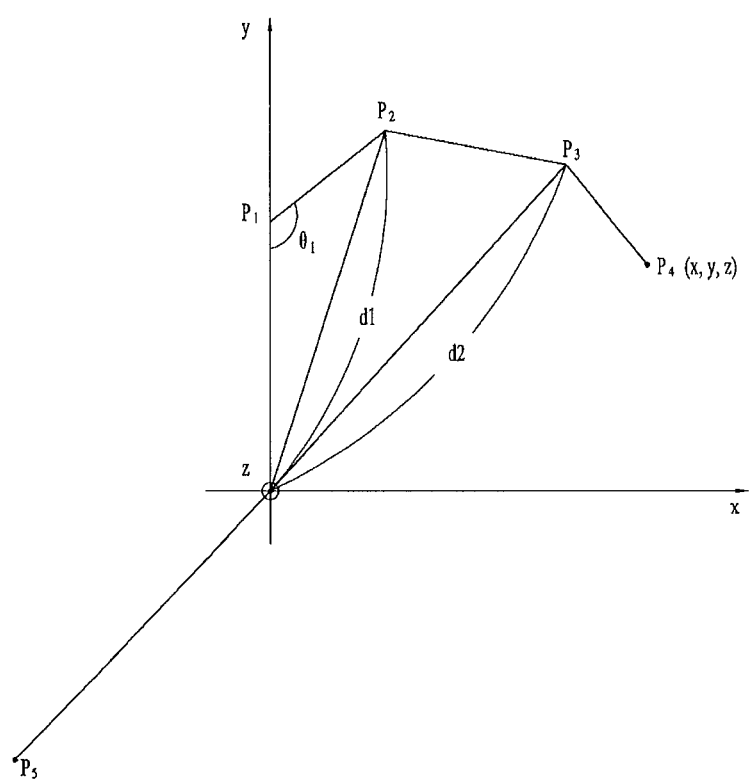
FIG. 7 is a view illustrating an operating process of the wearable device in accordance with one embodiment of the present invention.

FIG. 7 is a view illustrating an operating process of the wearable device in accordance with one embodiment of the present invention. In FIG. 7, x/y/z axes represent a 3D space and lines connecting the origin and points P1, P2, P3 and P4 represent a frame from a user's wrist to a finger if an object is a user's hand. That is, the origin represents the center of the wrist, the point P1 represents a joint connecting the palm to the first phalange of the finger, the point P2 represents a joint connecting the first phalange to the second phalange of the finger, the point P3 represents a joint connecting the second phalange to the third phalange of the finger, and point P4 represents the tip of the finger.

The wearable device may calculate the 3D position and bending angle of a joint connecting the first phalange to the second phalange of a user's finger. That is, the wearable device may calculate a 3D position of the point P2 and an angle $\theta 2$ in FIG. 6. Since the wearable device may generate and store a 3D model of a user's hand, calculation of the 3D position of the point P2 means calculation of a distance d1 from the center of the wrist to the point P2.

Similarly to the point P2, the wearable device may calculate a 3D position of the point P1 and an angle $\theta 1$. Otherwise, during the process of generating the 3D mode, the wearable device may calculate a distance from the center of the wrist to a joint between the palm and the first phalange, i.e., the position of the point P1, in advance. In this case, the wearable device may calculate the angle $\theta 1$ through comparison with the pattern in a similar manner as the angle $\theta 2$. That is, the wearable device may calculate the positions and bending angles of the respective joints by comparing change of the positions, sizes and external appearances of the blood vessels of the respective joints with the pre-stored pattern.

On the assumption that a user's finger is bent according to a natural motion, if the coordinates of the point P1, the coordinates of the point P2, and the angles $\theta 1$ and $\theta 2$ are given, all of the coordinates of the point P3, the angle $\theta 3$ and the coordinates of the point P4 may be calculated. Such a process may be carried out by an experimental method, i.e., estimation by experience. However, unless the user consciously bends finger joints by abnormal angles, the coordinates of the point P3 and the angle θ3 may be calculated with high precision from relations among the coordinates of the point P1, the coordinates of the point P2, and the angles θ1 and θ2. Further, similarly, the position information of the point P4 may be precisely calculated from relations among the coordinates of the point P1, the coordinates of the point P2, the coordinates of the point P3, and the angles θ1, θ2 and θ3.

In the above-described process, the ranges of the angles θ1, θ2 and θ3 may become an issue. That is, the angles θ1, θ2 and θ3 need to be within 180 degrees. If a user raises a finger highly, a joint connecting the user's palm and the first phalange of the finger may be 180 degrees or more. However, such an angle is far from a normal key input motion. Therefore, during a process of measuring the angles θ1, θ2 and θ3 of the joints, the wearable device may acquire only values of angles which are within 180 degrees as significant values. The wearable device may be implemented so as to ignore values of the angles θ1, θ2 and θ3 which are greater than 180 degrees, or to map the angles θ1, θ2 and θ3 which are greater than 180 degrees to a specific motion.

There are various methods to improve precision in such an estimation process. For example, after generation of the 3D model of a hand is initially carried out, the wearable device may instruct a user to perform a motion to input a specific key. When the user makes a natural motion to input the corresponding key, the wearable device may sense such a motion and foreknow which value needs to be compensated for during the estimation process of the point P3, the point P4 and the angle θ3. That is, software compensation may be carried out during a process of calculating an input value according to a user's key input motion.

In another method, the wearable device may directly measure the 3D position of the point P3 and the angle θ3. That is, the optical signal sensing unit and the data processor may compare blood vessels around the joint connecting the second phalange to the third phalange of a finger with the pattern of the 3D model and thus measure the 3D position and bending angle of the corresponding joint. In this case, since the wearable device directly measures the points P1, P2 and P3, the angles θ1, θ2 and θ3 and a distance d2, precision in estimation of the point P4 is greatly raised. Otherwise, the above-described software compensation method may be carried out together with the method of directly measuring the point P3 and the angle θ3.

Consequently, as a user performs typing, the wearable device senses a key input motion, judges a key to which the corresponding key input motion corresponds, and generates an input value. Such an input value may be transmitted to an external device or a server connected to the wearable device and the wearable device is operated as an input unit.

The embodiment in which the wearable device senses key input motions of the forefinger, the middle finger, the ring finger and the little ringer of a user's hand has been described above. Further, the wearable device needs to sense a key input motion of the thumb. The wearable device may estimate the location of the thumb on which the wearable device is mounted from the locations of the joints of four other fingers. That is, the wearable device may estimate a 3D location of the thumb from P1 and P2 locations of four other fingers. When the wearable device estimates the location of the thumb by using P1 or P2, P1 or P2 of fourth fingers, that is, four positional information is used and when the wearable device estimates of the location of the thumb by using the P1 and P2, the wearable device estimates the location of the thumb b using 8 positional information. That is, since the wearable device has information on the sufficient number for specifying the location of the thumb in the 3D space, the wearable device may estimate the location of the thumb from positional information of the joints of four other fingers.

Differently from the other four fingers, the thumb includes a joint connecting the palm and the first phalange and a joint connecting the first phalange and the second phalange, i.e., two joints. That is, even if the wearable device acquires the positions of the two joints, the wearable device may measure the position of the tip of the thumb. Therefore, if the wearable device is worn on any other finger instead of the thumb, the point P3 measured from the points P1 and P2 and the angles θ1 and θ2 becomes the position of the tip of the thumb. Thereby, the wearable device may measure the position of the tip of the thumb with higher precision than the other four fingers.

Hereinabove, the embodiment has been described, in which the wearable device senses the blood vessel at the joint part of the finger, compares the sensed blood vessel with the prestored bio pattern and blood vessel pattern, and senses the motion of the finger of the user to calculate the 3D location of the end of the finger. As described above, the 3D location of the end of the finger matches a predetermined 3D coordinate value and the wearable device may verify what gesture the hand of the user takes from the 3D location of the finger. Subsequently, the wearable device may execute or perform an operation or command which matches the gesture by recognizing the verified gesture.

Hereinafter, differently from the above description, an embodiment in which the wearable device senses blood vessels around phalanges of a finger will be described. That is, the wearable device may detect the 3D position of the tip of the finger by sensing blood vessels at the phalanges of the finger as well as the joints of the finger. For example, the wearable device may sense the position P1 and angle θ1 of the joint connecting the palm (or the back) and the first phalange of the finger by sensing the arrangement and distribution of blood vessels of the palm and the first phalange of the finger, and sense the position P2 and angle θ2 of the joint connecting the first phalange and the second phalange of the finger by sensing blood vessels of the first phalange and the second phalange of the finger. The above-described embodiment may be similarly applied to a process of estimating the position of the tip of the finger by measuring the positions of the two joints.

Further, even if the wearable device senses only one phalange of a finger, the wearable device may sense the position of a joint. That is, the pattern information of blood vessels added to the 3D model may be 3D information and thus include information regarding the thickness and the slope of the blood vessel, the blood vessel pattern, and the bio pattern, as described above. Therefore, the wearable device may detect positions of other joints by sensing blood vessels from a single phalange of a finger and comparing the sensed blood vessel information with the pre-stored pattern. In connection with such an embodiment, as a finger is bent, not only the arrangement and positions of blood vessels but also brightness and chroma of the blood vessels are changed. That is, as a finger is bent, the confirmed external appearances of blood vessels are changed, i.e., flesh of the finger is folded or wrinkles are made. Accordingly, the wearable device may detect the position of the tip of the finger in overall consideration of sensed transparency, brightness, chroma and the like of the blood vessels.

Hereinabove, the embodiment has been described, in which the wearable device estimates the 3D coordinate of the end of the finger from the locations of the joints of the hand of the user in association with FIG. 7. The embodiment is extended to be appreciated as an embodiment of estimating the spatial location of the entire lower arm of the user.

When described in detail, the original point of FIG. 7 represents the center of the wrist of the user. In this case, the wearable device may measure an angle formed by the hand and the lower arm of the user. That is, the wearable device may measure angles at which the hand and the lower arm of the user are bent, degrees at which the hand and the lower arm of the user rotate, and the like by using the bio pattern recognizing unit or the depth sensor. When it is considered that the palm, the back of the hand, and the lower arm of the user are relatively flat, the wearable device may recognize the straight line from the original point to P5 of FIG. 7 as the lower arm of the user. Therefore, the wearable device may recognize the 3D coordinates of the hand and the fingers of the user according to the aforementioned embodiments and also recognize the angle and the location of the lower arm connected with the hand. Moreover, since the wearable device may measure the blood vessel data from the configuration of the optical signal transmission unit/optical signal sensor, the wearable device may determine the accurate location and form of the hand of the user by adding the blood vessel data to the angle and the location of the lower arm.

Furthermore, the wearable device measures the location, the bending angle, the rotation degree, and the like of the joint of the elbow by the similar method to the aforementioned embodiments to determine the spatial location and the form of the upper arm connected with the lower arm. The aforementioned embodiments are integrated, and as a result, the wearable device may measure all of the spatial locations, the spatial layout forms, the rotation degrees, and like of a series of bodily structures connected to the shoulder, the elbow, the wrist, the joint of the palm, and the joints of the finger.

Figure 8:
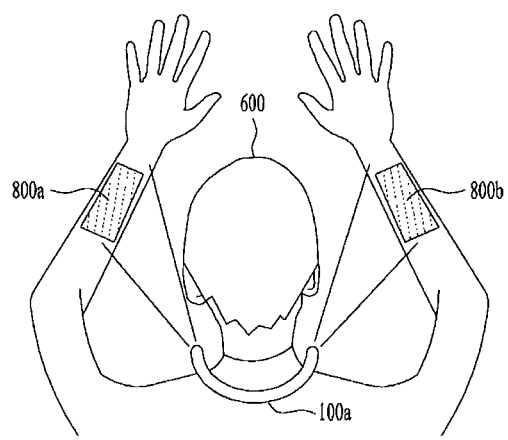
FIG. 8 is a view illustrating an operating process of the wearable device in accordance with one embodiment of the present invention.
Figure 8:
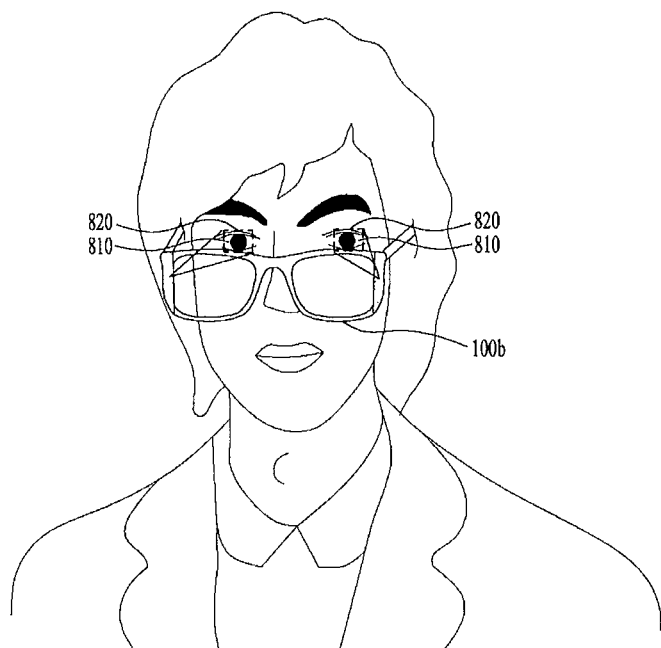

FIG. 8 is a view illustrating an embodiment in which the wearable device transmits the output to the outside. FIG. 8(*a*) illustrates an embodiment in which the wearable device 100*a* implemented in a neck wear form outputs an image to both arms of the user. FIG. 8(*b*) illustrates an embodiment in which the wearable device 100*a* implemented in a spectacle form outputs an image to eyes of the user.

First, the wearable device may output the image to the fixed location, at the fixed angle, and with the fixed size as described in FIG. 1 above. For example, in FIG. 8(*a*), the wearable device 100*a* measures the 3D coordinate of the arm which is the object to know the coordinate, the form, and the angle of the arm positioned in the space. Subsequently, the wearable device 100*a* may output the image by fixing the image to both arms which are the objects by controlling the size and the angle to output the image (800*a* and 800*b*). Since the wearable device may continuously measure the 3D coordinate of the arm, the wearable device 100*a* may continuously output the image at the fixed location and the fixed angle even though the user moves the arm.

For example, when the arm of the user moves while the wearable device outputs the image, physical characteristic values including the layout, the distribution, the angle, and the like of the blood vessel sensed from the object vary. As a result, the wearable device newly calculates the spatial coordinate (the location, the angle, the form, and the like) of the arm of the object to fixedly output the image.

Further, the wearable device may measure the movement direction, the movement angle, and the movement speed of the wearable device by using the acceleration sensor and the gyroscope sensor. Accordingly, even though the body of the user slightly moves in the wearable device implemented in the neck wear form, the wearable device may control the output location and angle of the image by reflecting measurement values of sensors. That is, physical measurement values for movement of the wearable device, which are measured by the acceleration sensor and the gyroscope sensor may be used for a compensation process for the location and the angle while outputting the image.

As another example, the wearable device foreknows information regarding the image, which the wearable device outputs, and may thus use the information. That is, the wearable device may calculate the size and angle of the image projected at a designated distance, sense the image actually projected onto the object as the reflected optical signal of visible light, and calculate a difference therebetween. The wearable device may detect relative position and angle relations between the object and the wearable device by compensating for such a difference.

As another example, the wearable device may fixedly output the image using the above-described depth sensor instead of sensing of reflected optical signal. That is, the wearable device may use a patterned optical signal during a process of sensing the object using the depth sensor through two methods. In more detail, the wearable device foreknows the transmission time and frequency band of the patterned optical signal and may thus foreknow the reception time of the optical signal. In this case, the depth sensor of the wearable device may calculate the distance and angle of the wearable device from the object from pre-stored information regarding the time and information regarding the frequency band. On the other hand, although the wearable device does not know information regarding the optical signal, the wearable device may receive the optical signal using a unit to selectively sense wavelength bands of the patterned optical signal.

As yet another example, the wearable device may output a predetermined pattern added to the edge of the image, as exemplarily shown in this figure. Such a pattern differs from the above-described pattern of blood vessels and means a marker added to the circumference of the image or a distinguishable indicator. The wearable device may transmit the image, to which such a pattern is added, and thus analyze the shape, size, tilt degree, distortion degree of the pattern projected onto the object, thereby detecting the distance, angle and positional relations between the object and the wearable device.

Meanwhile, the wearable device may adjust the output image while outputting the image to the arm of the user. The adjustment may include all of a color adjusting process of adjusting the color, the chroma, and the brightness of the image and a form adjusting process of adjusting extension, contraction, rotation, distortion, and the like of the image. The color adjusting process and the form adjusting process may be performed by considering at least one of the blood vessel pattern and the bio pattern.

When described in detail, in the case where the wearable device outputs the image onto a skin surface such as the arm of the user, a skin color of the user individually varies. The skin color is widely distinguished into a block color, a yellow color, and a white color, but in more detail, the skin color has different color values in all persons. Accordingly, the wearable device may perform the color adjusting process with respect to the output image in order to express the image output by the wearable device as a predetermined color, chroma, and brightness regardless of the skin color. For example, since the wearable device premeasures the color, chroma, and brightness values through the bio pattern recognizing unit, the wearable device may adjust the color, the chroma, and the brightness of the image to be output by considering the color, the chroma, and the brightness of the skin which is the location to which the image will be output. According to such a process, the user may verify a predetermined image regardless of the color of the skin.

Further, the wearable device may perform the form adjusting process in order to output the image to the fixed location with the fixed size. For example, in the case where the image is output to the periphery of the joint of the wrist, when the joint of the wrist is bent, the image is naturally distorted. In this case, the wearable device may accurately provide a desired image to the user only by geometrically adjusting the image by considering a degree in which the joint of the wrist is bent. Accordingly, the wearable device may adjust the form of the output image by considering the spatial location, the form, the curve, the rotation degree, and the like of the object. For example, the wearable device may extend a part of the image to be output to a part which is bent to be concave and contract and output a part of the image to be output to a part which is projected to be convex. Further, the wearable device may adjust the border of the image along a boundary line of the part to which the image will be output. For example, when the boundary line of the part to which the image will be output is a circle, the wearable device may accurately provide the desired image to the user by adjusting the border of the image according to the circular boundary line.

Meanwhile, in FIG. 8(b), the wearable device 100b outputs the image to eyes 810 of the user. Through the embodiment, the user may experience the augmented reality (AR) in which the image output by the wearable device 100b overlaps with the thing viewed by the user. That is, FIG. 8(b) illustrates the VRD method among the wearable, AR/VR device, HMD, and OHMD concepts described in FIG. 1 above.

According to the illustrated embodiment, an embodiment may be considered, in which the wearable device 100b does not directly output the image to the eyes 810, but outputs the image onto glasses of the spectacles. Further, when the wearable device 100b combines the actual thing and the virtual image by reflecting the image instead of directly outputting the image to the eyes 810 of the user (AR), an embodiment to which the waveguide technology is applied is provided. Even in any case, since an embodiment in which the image is output in the line-of-sight direction and the user may thus experience the AR is provided, the VRD method is representatively described as an example. In detail, the wearable device may output the image so that the user experience the augmented reality for the arm by outputting the image to the eyes of the user instead of directly outputting the image to the arm as illustrated in FIG. 8(a). For such a process, the wearable device precalculates all of the 3D coordinates of the arm which is the location to which the object will be output and the angle in the space, the rotation degree, and the like. Subsequently, the wearable device calculates the distance and the angle up to the location to which the object will be output from the eyes of the user. The wearable device implemented in the spectacle form is positioned to be close to the eyes of the user. Therefore, the wearable device may acquire the distance to and the angle of the location to which the object will be output from the eyes of the user through a simple compensation process with respect to the distance to and the angle of the location to which the object will be output therefrom.

The wearable device which calculates the distance to and the angle of the object measures the distance to and the angle of the eyes of the user to which the image will be actually output to calculate how the distance and the angle are compensated when the calculated values are output to the eyes of the user. For example, the size, the angle, the distortion degree, the color, and the like which are the physical characteristic values of the image need to be adjusted and the wearable device outputs the image to the eyes of the user according to the adjusted values. As a result, the user feels as if the image is actually output to the corresponding location while viewing the arm of the user.

The advantage of the embodiment is that a 3D effect image may be provided to the user unlike actually outputting the image to the arm. The user performs various types of interactions to be described below to visually verify an immediate feedback for the augmented reality.

Meanwhile, unlike the embodiment of FIG. 8(b), the wearable device 100b implemented in the spectacle form may also directly output the image to the arm of the user. That is, the wearable device 100b outputs the image to an opposite side to the eyes of the user to output the image to the arm of the user or to the outside.

Although not illustrated, according to yet another embodiment, the wearable device may be implemented in the cap form or the helmet (alternatively, the head mount display) form. In the embodiment, the wearable device transmits the optical signal to the face of the user and senses the reflection optical signal to acquire the blood vessel data of the face of the user. As a result, when the wearable device outputs the image to the eyes of the user, the wearable device analyzes the blood vessel data of the face to output the image to the fixed location with the fixed size. Accordingly, even though the user walks or runs and the wearable device slightly swings, the image may be stably output to the fixed location. Further, even in the cap form or the helmet form, the wearable device may output the image in an opposite direction to the face of the user, such as the arm of the user, and the like, of course. In addition, the wearable device may fix and output the image to a large portion of the face of the user. That is, the wearable AR/VR device or the wearable device implemented as the HMD and the OHMD has advantages to output the image onto the line-of-sight of the user and to output the image to all surfaces of the face of the user. Further, since the wearable device outputs the image by using the vein pattern or the bio pattern, the wearable device may fixedly output the image in spite of the motion of the user similarly as described above.

Figure 9:
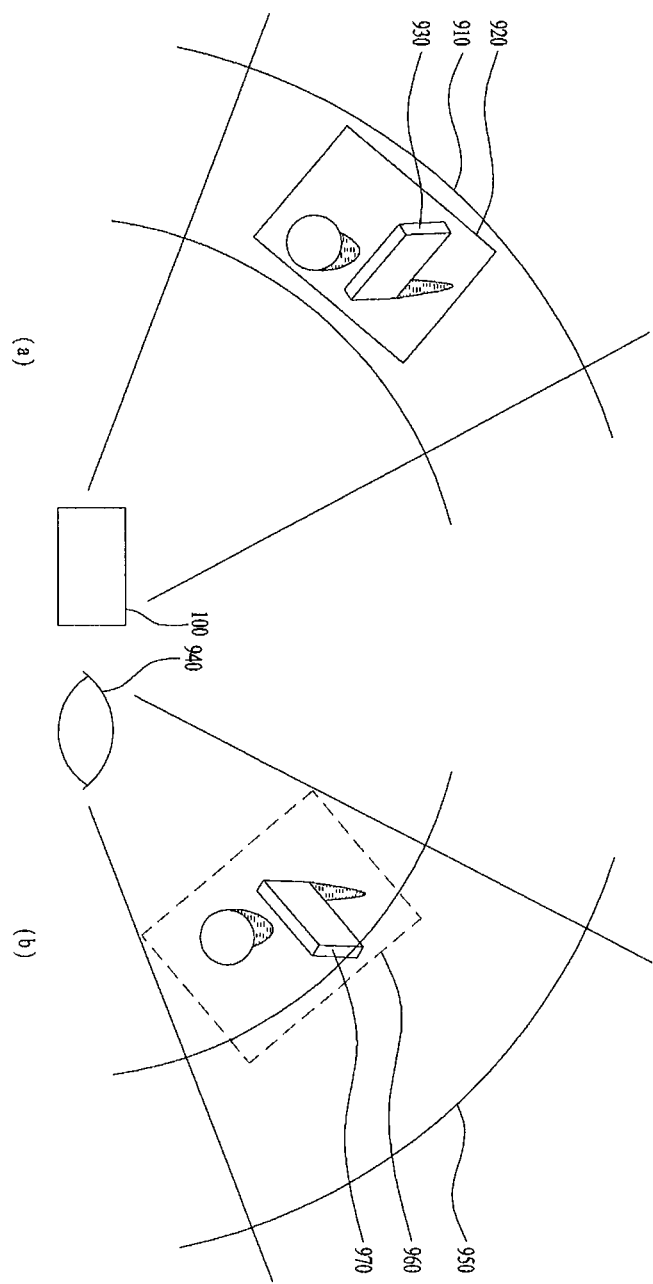
FIG. 9 is a view illustrating an operating process of the wearable device in accordance with one embodiment of the present invention.

FIG. 9 is a view illustrating an embodiment in which the wearable device provides the AR service to the user. In FIG. 9, a case where the image output in FIG. 8(a) is the AR service is materialized.

Figure 10:
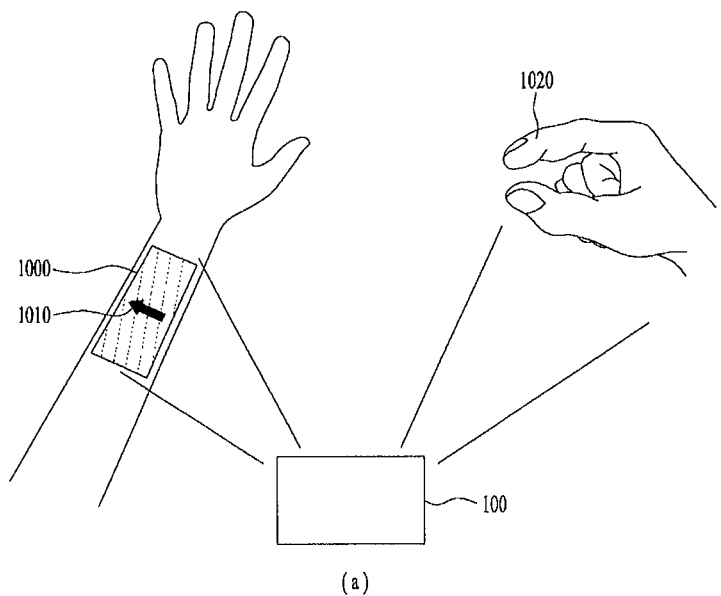
FIG. 10 is a view illustrating an operating process of the wearable device in accordance with one embodiment of the present invention.
Figure 10:
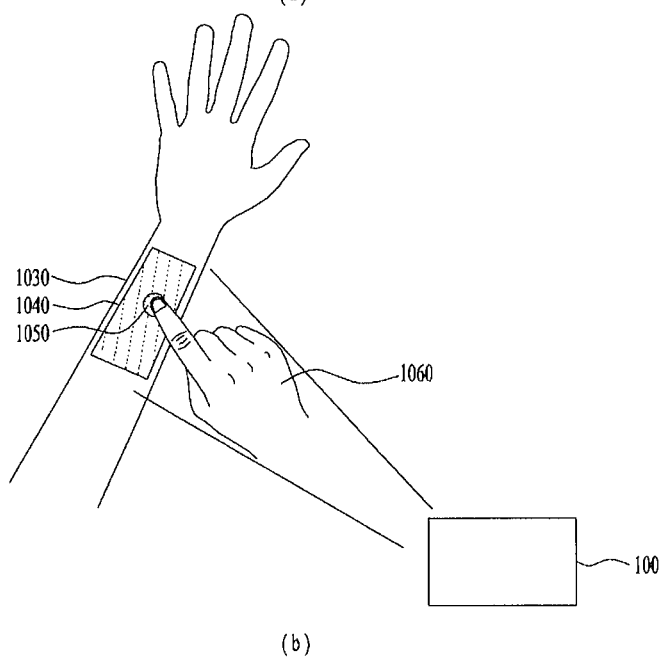

First, FIG. 9(a) illustrates an embodiment in which the wearable device 100 outputs an image 920 to a left arm 910 of the user. In FIG. 9(a), the image 920 output to the left arm 910 of the user includes 3D objects 930. Accordingly, the user may experience the AR in which the 3D objects 930 are combined to the body of the user and in this case, the left arm 910 of the user becomes a user interface in which the image 920 is output. In FIG. 10, when a light touch method to be described below is adopted, the left arm 910 of the user serves as an input interface as well as an output interface.

In the embodiment of FIG. 9(a), the wearable device 100 continuously scans the vein pattern and the bio pattern of the user to fix the location to which the image 920 will be output. That is, since the wearable device 100 may determine the location by distinguishing the components of the body of the user by the unit of the joint, the wearable device 100 may continuously track the location of the left arm 910 in spite of the motion of the left arm 910 of the user. Accordingly, the image 920 is output to the fixed location, and as a result, the wearable device 100 may stably provide the AR service to the user.

In FIG. 9(a), an embodiment is described, in which the image 920 is directly output onto the surface of the left arm 910 of the user. FIG. 9(b) illustrates an embodiment in which the image is not output to a right arm 950 of the user but an image 960 is output to a virtual space. In FIG. 9(b), the wearable device outputs the image 960 in the line-of-sight direction from eyes 940 to the right arm 950 of the user. That is, the image 960 output by the wearable device may be fixed and output onto a space spaced apart from the right arm 950 like a hologram. When the image 960 is fixed and output onto the space based on the right arm, the user may recognize as if a 3D object 970 on the image 960 also floats in the air:

FIG. 10 is a view illustrating an operation of the wearable device depending on the motion of the user. FIG. 10(a) illustrates a space mouse concept and FIG. 10(b) is a diagram for describing a light touch concept.

First, in FIG. 10(a), the wearable device 100 outputs the image to the left arm of the user (1000). Subsequently, the wearable device 100 may sense that the right arm of the user performs the mouse movement operation or the mouse click operation and operate as a space mouse. In detail, when the image which is being output is contents to support movement or click of the mouse, a mouse cursor 1010 output to the image moves as a right hand 1020 of the user moves in the space. It may be appreciated that in such a process, an operation in which the wearable device 100 measures the 3D coordinate of a left hand of the user to output the image with the fixed size and at the fixed angle is performed and an operation in which the wearable device 100 measures the 3D coordinate of a right hand of the user to track the spatial motion of the right hand is simultaneously performed. That is, the wearable device measure the blood vessel pattern and the bio pattern of the right hand 1020 to track the 3D coordinate and the spatial motion of the right hand 1020 and thus, output the 3D coordinate and the spatial motion while moving the mouse cursor 1010. A process in which the wearable device 100 measures the blood vessel pattern and the bio pattern of the right hand may be performed through a process in which the blood vessel distribution and the bio characteristic (visually verified characteristics including the crease, the lines of the palm, and the like) are sensed by using the optical signal transmission unit/optical signal sensor, the bio pattern recognizing unit, and the depth sensor.

Subsequently, when the user takes the mouse click operation in which a forefinger or a middle finger contacts a thumb during the mouse moving operation, the wearable device 100 senses the mouse click operation. Subsequently, the wearable device 100 executes a left click or right click command corresponding to a point where the mouse cursor 1010 is positioned in the image which is being output.

Meanwhile, a process in which the wearable device 100 measures the motion of the right hand of the user may be just achieved by a process in which the 3D coordinate of the right hand is continuously tracked. Unlike this, the wearable device 100 may measure the motion of the right hand as a relative value from the left hand by considering that the left hand of the user is slightly fixedly positioned for output 1000 of the image. That is, the wearable device 100 may track the motion of the right hand as the relative value by considering the direction in which and the angle at which the right hand of the user moves from the left hand (in particular, a point where the image is output). In this case, complexity of a calculation process for analyzing the mouse movement operation may be reduced.

Subsequently, in FIG. 10(b), the wearable device 100 outputs an image 1040 to a left arm 1030 of the user. In this case, the user touches a specific point 1050 on the image 1040 output to a right hand 1060. An embodiment in which the user directly touches a specific part on the output image as described above is referred to as light touch and hereinafter, the light touch will be described in detail.

The wearable device 100 measures a location 1050 touched by the right hand 1060 of the user to sense an interaction associated with the output image 1040. For example, the wearable device 100 may sense a light touch operation in which the user selects any one of the output applications while outputting icons associated with various applications. When an operation of touching a specific icon is sensed, the wearable device 100 may execute the application corresponding to the relevant icon.

In such a process, it is very important that the wearable device 100 accurately determines the location corresponding to the light touch of the user. The wearable device 100 may generally sense the light touch operation of the user through two methods.

First, the wearable device 100 senses the right hand 1060 itself of the user to sense the light touch operation. In other words, the wearable device 100 that continuously tracks the right hand 1060 of the user may recognize that the light touch is performed when the 3D coordinate of the end of the finger performing the light touch in the right hand of the user is close to a coordinate of the surface of the left hand of the user. For example, when the 3D coordinate of the end of the finger of the right hand of the user is close to the coordinate of the surface of the left hand of the user by a value less than a threshold value, the wearable device 100 may recognize that the light touch operation is achieved.

As yet another example, since the light touch operation has already been sensed during the process of outputting the image 1040, the wearable device 100 may easily know which location in the image 1040 the 3D coordinate of the end of the finger of the right hand of the user indicates. In other words, the wearable device 100 determines a part covered by the light touch operation of the user in the image output thereby to recognize the light touch operation corresponding to the contact location.

According to the embodiments described above, the wearable device may calculate the 3D coordinate in the space according to various operations of the user and provide an enhanced service to the user through a subsequent processing procedure. However, the aforementioned embodiments are not particularly limitedly applied only to the wearable device. That is, the components and operating processes may be implemented as not only a form which is mounted on the user but also an independent device (that is, a non-wearable device).

It will be apparent to those skilled in the art that various modifications and variations can be made in the present invention without departing from the spirit or scope of the invention. Thus, it is intended that the present invention cover the modifications and variations of this invention provided they come within the scope of the appended claims and their equivalents.

What is claimed is:

1. A device comprising:
a signal transmission unit configured to transmit signals;
a signal sensing unit configured to receive reflected signals, wherein the reflected signals represent at least the transmitted signals reflected by blood vessels in a body part of a user;
one or more processors configured to:
generate blood vessel data based on the reflected signals, wherein the blood vessel data represents information associated with 3 dimensional (3D) locations of the blood vessels of the body part,
generate 3D coordinates from the blood vessel data, wherein the 3D coordinates represent a location of the body part,
determine a line of sight representing a viewing direction, an orientation or a combination thereof of the user, and
generate an image according to the line of sight; and
an image output unit operably coupled to the one or more processors and configured to output the image according to the 3D coordinates and the line of sight, wherein the image is displayed at a display location associated with the 3D coordinates.

2. The device of claim 1, wherein the one or more processors are further configured to generate the 3D coordinates based on matching the blood vessel data to a 3D model or a portion thereof, wherein the 3D model represents previously determined locations, relative arrangements, or a combination thereof of blood vessels within one or more body parts of the user.

3. The device of claim 2, wherein the one or more processors are further configured to identify the body part based on the reflected signals, the blood vessel data, or a combination thereof.

4. The device of claim 3, wherein the one or more processors are further configured to identify the body part based on matching the blood vessel data to a portion of the 3D model associated with the body part, wherein the 3D model represent connection patterns and relative locations of the blood vessels in 3D for one or more body parts of the user.

5. The device of claim 3, wherein the one or more processors are further configured to:
determine a degree of distortion based on comparing the blood vessel data and the 3D model, wherein the 3D model includes values representing (1) distances between portions within the body part, (2) locations of joints between the portions, (3) angular patterns of the portions about the joints corresponding to movements of the portions, (4) joint movement ranges corresponding to range of movements about the joints, or a combination thereof relative to the blood vessels of the body part; and
determine a physical state based on the degree of distortion, the physical state for describing a location, a shape, a curve, or a combination thereof of the body part or one or more portions thereof.

6. The device of claim 3, wherein the one or more processors are further configured to distinguish the body part from inanimate objects captured by the reflected signals based on the blood vessel data.

7. The device of claim 2, wherein the one or more processors are further configured to generate a second coordinate based on the 3D model and the 3D coordinates of the body part, wherein the second coordinate represents a spatial location of a portion within the body part.

8. The device of claim 7, wherein:
the 3D coordinates represent a location of an arm, a hand or a combination thereof; and
the second coordinate represents a finger, a fingertip, or a combination thereof.

9. The device of claim 1, wherein the image output unit is configured to display the image for an augmented reality application or a virtual reality application.

10. The device of claim 1, wherein the one or more processors are further configured to:
identify bio markers based the reflected signals, wherein the bio markers represent visible features on a surface of the body part; and
adjust the image according to the bio markers for displaying the image overlapping the surface of the body part.

11. The device of claim 1, wherein:
the one or more processors are further configured to calculate the display location as a fixed location relative to the 3D coordinates; and
the image output unit is configured to display the image at the display location for maintaining the fixed spatial relationship between the 3D coordinates and the display location.

12. The device of claim 11, wherein the one or more processors are further configured to calculate the display location independent of motion, location, or a combination thereof of the device.

13. The device of claim 1, wherein the one or more processors are further configured to:
generate a second coordinate representing a second body part;
determining an input value based on the display location and the second coordinate.

14. The device of claim 13, wherein the one or more processors are further configured to:
calculate the display location for presenting the image relative to a first arm or a portion thereof;
wherein:
the second coordinate represents a location of a hand or a fingertip connected to a second arm; and
the input value represents a user selection.

15. A method of operating a device, the device having a signal transmitter and a signal receiver, the method comprising:
operating the signal transmitter to transmit signals;
receiving reflected signals using the signal receiver, wherein the reflected signals represent at least the transmitted signals reflected by blood vessels in blood vessels in a body part of a user;
generating blood vessel data based on the reflected signals, wherein the blood vessel data represents information associated with 3 dimensional (3D) locations of the blood vessels of the body part;
generating 3D coordinates from the blood vessel data, wherein the 3D coordinates represents a location of the body part;
determining a line of sight for representing a viewing direction, an orientation or a combination thereof of the user;
generating an image according to the line of sight; and
outputting the image according to the 3D coordinates, wherein the image is displayed at a display location that is fixed relative to the 3D coordinates.

16. The method of claim 15, wherein:
generating the 3D coordinates includes matching the blood vessel data to a 3D model or a portion thereof, wherein the 3D model represents:
  previously determined locations, relative arrangements, or a combination thereof of blood vessels within one or more body parts of the user, and
  relative to the blood vessels of the body part, (1) distances between portions within the body part, (2) locations of joints between the portions, (3) angular patterns of the portions about the joints corresponding to movements of the portions, (4) joint movement ranges corresponding to range of movements about the joints, or a combination thereof;
further comprising:
determining a degree of distortion based on comparing the blood vessel data and the 3D model; and
determining a physical state based on the degree of distortion, the physical state for describing a location, a shape, a curve, or a combination thereof of the body part or one or more portions therein.

17. The method of claim 16, further comprising:
generating a second coordinate based on the 3D model and the 3D coordinates of the body part, wherein:
the 3D coordinates represent a location of an arm, a hand or a combination thereof; and
the second coordinate represents a location of a finger, a fingertip, or a combination thereof.

18. A tangible, non-transitory computer-readable medium having instructions encoded thereon that, when executed by one or more processors, causes the one or more processors to:
transmit signals;
receive reflected signals, wherein the reflected signals represent at least the transmitted signals reflected by blood vessels in blood vessels in a body part of a user;
generate blood vessel data in based on the reflected signals, wherein the blood vessel data represents information associated with 3 dimensional (3D) locations of the blood vessels of the body part;
generate 3D coordinates from the blood vessel data, wherein the 3D coordinates represent a location of the body part;
determine a line of sight representing a viewing direction, an orientation or a combination thereof of the user;
generate an image according to the line of sight; and
output the image according to the 3D coordinates and the line of sight, wherein the image is displayed at a display location associated with the 3D coordinates.

* * * * *